US006187805B1

(12) United States Patent
Pineiro et al.

(10) Patent No.: US 6,187,805 B1
(45) Date of Patent: Feb. 13, 2001

(54) INDOLE AND INDOLINE DERIVATIVES AS 5-HT$_6$ SELECTIVE LIGANDS

(75) Inventors: Jose Luis Castro Pineiro; George Mc Allister, both of Bishops Stortford; Michael Geoffrey Neil Russel, Welwyn Garden City, all of (GB)

(73) Assignee: Merck Sharp & Dohme Ltd., Hoddesdon (GB)

( * ) Notice: Under 35 U.S.C. 154(b), the term of this patent shall be extended for 0 days.

(21) Appl. No.: 09/392,406

(22) Filed: Sep. 9, 1999

(30) Foreign Application Priority Data

Sep. 15, 1998 (GB) .................................................. 9820113

(51) Int. Cl.$^7$ ...................... A61K 31/405; A61K 31/445; A61K 31/495; C07D 209/04; C07D 401/00
(52) U.S. Cl. .......................... 514/415; 514/414; 514/323; 514/235.2; 514/253; 548/469; 548/491; 548/467; 546/201; 544/143; 544/373
(58) Field of Search ..................................... 548/469, 491, 548/467; 514/415, 414, 323, 235.2, 253; 546/201; 544/143, 373

(56) References Cited

U.S. PATENT DOCUMENTS

| 3,481,953 | 12/1969 | Herbst et al. . |
| 3,489,429 | 1/1970 | Herbst et al. . |
| 5,696,122 | * 12/1997 | Gaster et al. ........................ 514/254 |

FOREIGN PATENT DOCUMENTS

| 0 815 861 | 1/1998 | (EP) . |
| WO 98/27058 | 6/1998 | (WO) . |
| WO 98/27081 | 6/1998 | (WO) . |
| WO 99/47516 | 9/1999 | (WO) . |

OTHER PUBLICATIONS

Fuji et al, CA118:101757, 1993.*
Bowman, et al, J. Chem. Soc. Perkin Trans. I, 1972, 1121–1123.
Bowman, et al, J. Chem. Soc., Perkin Trans I, 1973, 438–442.
Cannon, et al, J. Med. Chem., 1984, 27, 386–389.
Castro, et al, J. Mdc. Chem., 1994, 37, 3023–3032.
Hoyer, et al, Pharmacol. Rev., 1994, 46, 157–204.
Kozikowski, et al, J. Org. Chem., 1980, 45, 3350–3352.
Persons, et al, Eur. J. Med. Chem., 1991, 26, 473–475.
Sleight, et al, Serotonin ID Research Alert, 1997, 2(3), 115–118.
Sleight, et al, Drug News Perspectives, 1997, 10, 214–224.
Sleight, et al, Br. J. Pharmacol., 1998, 124, 556–562.
Spadoni, et al, J. Med. Chem., 1993, 36, 4069–4074.
Chem Pharm. Bull. 40(9) 2344 (1992), Masahiro Fuji, Hideake Murtake, and Mitsutaka Natsume.

* cited by examiner

Primary Examiner—Deborah C. Lambkin
(74) Attorney, Agent, or Firm—James L. McGinnis; David L. Rose

(57) ABSTRACT

Three classes of indole and indoline derivatives are disclosed as ligands selective for the 5-HT$_6$ receptors, and hence of value in the treatment or prevention of CNS disorders, including Alzheimer's disease, Parkinson's disease, schizophrenia, depression and anxiety. A particular class, 1-substituted-4-(ω-N,N-dialkyl-aminoalkyl)indoles, are claimed as novel compounds.

19 Claims, No Drawings

INDOLE AND INDOLINE DERIVATIVES AS 5-HT$_6$ SELECTIVE LIGANDS

FIELD OF THE INVENTION

The present invention relates to classes of indole derivatives which bind selectively to 5-HT$_6$ receptors, and hence are potentially useful in the treatment of a number of clinical conditions believed to be sensitive to the selective agonism or antagonism of the 5-HT$_6$ receptors. Certain of the compounds are novel.

BACKGROUND OF THE INVENTION

The actions of the neurotransmitter 5-hydroxytryptamine (5-HT) are mediated through a number of receptor families termed 5-HT$_1$, 5-HT$_2$, 5-HT$_3$, 5-HT$_4$, 5-HT$_5$, 5-HT$_6$, and 5-HT$_7$ (see D. Hoyer et al., *Pharmacol. Rev.*, 1994, 46, 157–204). Although the functions of the 5-HT$_5$, 5-HT$_6$ and 5-HT$_7$ receptors are less well understood than the functions of the other 5-HT receptors, it is generally accepted that compounds which selectively interfere with 5-HT-mediated signal transduction are important novel drug targets. In particular, 5-HT$_6$ selective ligands have been identified as potentially useful in the treatment of certain CNS disorders such as Parkinson's disease, Huntingdon's disease, anxiety, depression, manic depression, psychosis, epilepsy, obsessive compulsive disorders, migraine, Alzheimers disease (enhancement of cognitive memory), sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such is IBS (Irritable Bowel Syndrome). (See WO98/27058, WO98/27081, Drug News Perspectives, 1997, 10, 214 and A. J. Sleight et al., *Serotonin ID Research Alert*, 1997, 2(3), 115–8).

A wide variety of 5-HT analogues incorporating an indole nucleus have been prepared and tested for pharmacological effects, but hitherto none has been shown to be a selective ligand for 5-HT$_6$ receptors. WO-A-98/27058 and WO-A-98/27081 disclose, respectively, sulphonamides and carboxamides which are 5-HT$_6$ receptor antagonists, but none of the compounds disclosed comprises an indole or indoline nucleus. Similarly, certain benzenesulphonamides of non-indole nature are disclosed as selective 5-HT$_6$ antagonists in EP-A-815861 and in *Br.J.Pharinacol.*, 1998, 124, 556–562.

Many analogues of 5-HT are known, comprising a 1-acyl- or 1-arylsulphonyl-3-(2-aminoethyl) indole nucleus (see, for example, U.S. Pat. Nos. 3,481,953 and 3,489,429). Fused-ring analogues, such as trans-4-dimethylamino-1-(4-methylbenzenesulphonyl)-1,3,4,5-tetrahydrobenz[cd]indol-5-ol, are also known (*J.Chem.Soc., Perkin Trans. I*, 1973, 438–42). Analogues comprising a 4-(2-N,N-dialkylaminoethyl)indole nucleus, unsubstituted in the 1-position, have been shown to be dopamine agonists (*Eur. J. Med. Chem.*, 1991, 26, 473–5; *J. Med. Chem.*, 1984, 27, 386–9). However, the 1-substituted derivatives disclosed herein are believed to be novel.

SUMMARY OF THE INVENTION

The present invention, in a first aspect, provides the use of a compound, or a pharmaceutically acceptable salt or prodrug thereof, for the manufacture of a pharmaceutical composition for the treatment and/or prevention of clinical conditions for which selective agonism or antagonism of 5-HT$_6$ receptors is indicated, said compound being an indole or indoline derivative having a structure in accordance with Formula I, II or III:

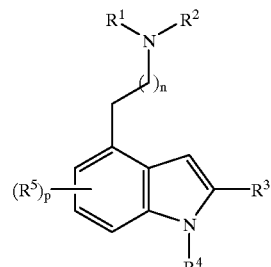

(I)

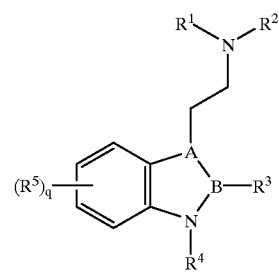

(II)

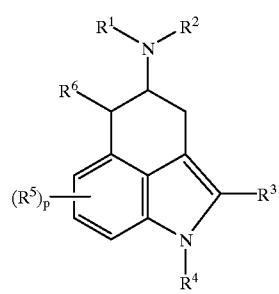

(III)

wherein
n is 1 or 2;
p is 0,1,2 or 3;
q is 0,1,2,3 or 4;
R$^1$ and R$^2$ independently represent hydrogen, C$_{1-6}$ alkyl or aryl (C$_{1-6}$)alkyl, or together represent the atoms necessary to complete a heterocycloalkyl group comprising the nitrogen atom to which R$^1$ and R$^2$ are attached;
R$^3$ represents hydrogen, C$_{1-6}$ alkyl, C$_{2-6}$ alkenyl, C$_{2-6}$ alkynyl, aryl(C$_{1-6}$)alkyl, aryl, heteroaryl, arylcarbonyl, heteroarylcarbonyl or C$_{1-6}$ alkylcarbonyl;
R$^4$ represents arylsulphonyl, heteroarylsulphonyl, C$_{1-6}$ alkylsulphonyl, di(C$_{1-6}$)alkylaminosulphonyl, arylcarbonyl, C$_{1-6}$ alkylcarbonyl, heteroarylcarbonyl or C$_{1-6}$ alkoxycarbonyl;
each R$^5$ independently represents hydroxy, C$_{1-6}$ alkoxy, aryl(C$_{1-6}$)alkoxy, nitrile or halogen;
R$^6$ represents hydrogen, hydroxy or C$_{1-6}$ alkoxy; and
-A-B- represents —C=C— or —CH—CH—.

Also in its first aspect, the invention further provides a method for the treatment and/or prevention of clinical conditions for which selective agonism or antagonism of 5-HT$_6$ receptors is indicated comprising administering to a patient in need of such treatment an effective amount of a compound in accordance with Formulae I, II or III, or a pharmaceutically acceptable salt or a prodrug thereof.

Compounds of Formula I wherein n,p, and $R^1$–$R^5$ are defined as before, and salts and prodrugs thereof, are novel and constitute a second aspect of the invention.

In its second aspect, the invention also provides a pharmaceutical composition comprising one or more compounds of Formula I, or pharmaceutically acceptable salts or prodrugs thereof, in association with a pharmaceutically-acceptable carrier.

Also in its second aspect, the invention further provides a compound of Formula I or a pharmaceutically acceptable salt or a prodrug thereof for use in therapy.

DETAILED DESCRIPTION OF THE INVENTION

The compounds of Formulae I–III are selective ligands for 5-$HT_6$ receptors, having a 5-$HT_6$ receptor (rat or human) binding affinity (Ki), when measured in cell lines expressing cloned recombinant 5-$HT_6$ receptors, of less than 1 $\mu$M, typically less than 100 nM, and in preferred embodiments less than 10 nM, and having a selective affinity for 5-$HT_6$ receptors relative to 5-$HT_5$ and/or 5-$HT_7$ receptors of at least 3-fold, typically at least 10-fold, and in preferred embodiments at least 100-fold.

In Formulae I–III, one or more substituents may be present on any alkyl or aryl group represented by any of $R^1$–$R^5$, or on any alkyl or aryl moiety of a group represented by anyi of $R^1$–$R^5$. Preferred substituents include $C_{1-6}$ alkyl, halogen, hydroxy and $C_{1-6}$ alkoxy.

As used herein, the expression "$C_{1-6}$ alkyl" includes methyl and ethyl groups, and straight-chained, branched or cyclic propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The term "halogen" as used herein includes fluorine, chlorine, bromine and iodine, especially chlorine or fluorine.

For use in medicine, the salts of the compounds of Formulae I–III will be pharmaceutically acceptable salts. Other salts may, however, be useful in the preparation of the compounds of Formulae I–III or of their pharmaceutically acceptable salts. Suitable pharmaceutically acceptable salts of the compounds of Formulae I–III include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of Formulae I–III carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope the use of prodrugs of the compounds of Formulae I–III above. In general, such prodrugs will be functional derivatives of the compounds of Formulae I–III which are readily convertible in vivo into the required compounds of Formulae I–III. Conventional procedures for the selection and preparation of suitable prodrug derivatives are described, for example, in *Design of Prodrugs*, ed. H. Bundgaard, Elsevier, 1985.

Certain compounds according to the present invention may be capable of existing as tautomeric forms. It is to be understood that all possible tautomers and mixtures thereof in any proportion are encompassed within the scope of the present invention.

Where the compounds according to the invention have at least one asymmetric centre, they may accordingly exist as enantiomers. Where the compounds according to the invention possess two or more asymmetric centres, they may additionally exist as diasterooisomers. It is to be understood that all such isomers and mixtures thereof in any proportion are encompassed within the scope of the present invention.

In Formulae I–III, suitable separate identities for $R^1$ and $R^2$ include hydrogen, methyl, ethyl, propyl and benzyl, and suitable identities for $R^1$ and $R^2$ in combination include pyrrolidinyl, piperidinyl, piperazinyl, 4-methylpiperazinyl and morpholinyl.

Suitable identities for $R^3$ include hydrogen, methyl, ethyl, benzyl, allyl, propargyl, benzoyl, phenyl, thienyl and furoyl.

Suitable identities for $R^4$ include benzenesulphonyl, naphthalene-2-sulphonyl, o-, m- or p-toluenesulphonyl, o-, m- or p-chlorobenzenesulphonyl, o-, m- or p-methoxy benzenesulphonyl, methanesulphonyl, dimethylaminosulphonyl, thienylsulphonyl, benzoyl, acetyl, furoyl and tert-butoxycarbonyl.

Suitable identities for $R^5$ include hydroxy, methoxy, ethoxy, propoxy, benzyloxy, nitrile, fluorine, chlorine and bromine. Preferably, there is no more than one $R^5$ substituent (i.e. p and q are 0 or 1), and when a single $R^5$ substituent is present, it, is preferably in the para-position relative to the indole nitrogen.

In the compounds of Formula I, p is preferably zero; $R^1$ and $R^2$ are preferably identical and represent hydrogen or methyl; $R^3$ preferably represents hydrogen or benzoyl; and $R^4$ preferably represents arylsulphonyl or dimethylaminosulphonyl. Examples of specific compounds in accordance with Formula I include:

2-[1-(benzenesulphonyl)-1H-indol-4-yl]ethylamine;
N,N-dimethyl 2-[1-(benzenesulphonyl)-1H-indol-4-yl] ethylamine;
N,N-dimethyl 2-[1-(dimethylamino)sulphonyl-1H-indol-4-yl]ethylamine;
N,N-dimethyl 3-[1-(benzenesulphonyl)-1H-indol-4-yl] propylamine; and
N,N-dimethyl 2-[1-(benzenesulphonyl)-2-benzoyl-1H-indol-4-yl]ethylamine.

In the compounds of Formula II, preferably $R^1$ and $R^2$ are identical and represent hydrogen or methyl, or together complete a pyrrolidinyl, piperidinyl, piperazinyl or 4-methylpiperazinyl ring; $R^3$ preferably represents hydrogen or methyl; $R^4$ preferably represents arylsulphonyl. thienylsulphonyl, benzoyl or tert-butoxycarbonyl; $R^5$ preferably represents hydroxy, methoxy, benzyloxy or nitrile; and q is zero or 1.

A sub-class of compounds in accordance with Formula II is defined by Formula II(a):

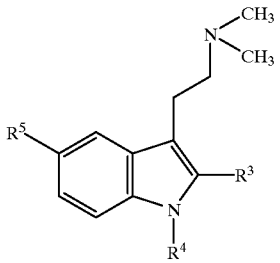

(II(a))

where $R^3$, $R^4$ and $R^5$ have the same meanings as before.

Specific examples of compounds in accordance with Formula II(a) include:

N,N-dimethyl 2-[1-(benzenesulphonyl)-5-methoxy-1H-indol-3-yl]ethylamine;

N,N-dimethyl 2-[5-methoxy-1-(4-methyl benzenesulphonyl)-1H-indol-3-yl]ethylamine;

N,N-dimethyl 2-[1-(4-chlorobenzenesulphonyl)-5-methoxy-1H-indol-3yl]ethylamine;

N,N-dimethyl 2-[1-(3-chlorobenzenesulphonyl)-5-methoxy-1H-indol-3-yl]ethylamine;

N,N-dimethyl 2-[5-methoxy-1-(2-naphthalenesulphonyl)-1H-indol-3-yl]ethylamine;

N,N-dimethyl 2-[5-methoxy-1-(4-methoxybenzenesulphonyl)-1H-indol-3-yl]ethylamine;

N,N-dimethyl 2-[1-(2-chlorobenzenesulphonyl)-5-methoxy-1H-indol-3-yl]ethylamine;

N,N-dimethyl 2-(1-benzoyl-5-methoxy-1H-indol-3-yl)ethylamine;

N,N-dimethyl 2-[5-methoxy-1-(2-thiophenesulphonyl)-1H-indol-3-yl]ethylamine;

N,N-dimethyl 2-(1-benzenesulphonyl-5-methoxy-2-methyl-1H-indol-3-yl)ethylamine;

N,N-dimethyl 2-(1-benzenesulphonyl-1H-indol-3-yl)ethylamine;

N,N-dimethyl 2-(1-methylsulphonyl-1H-indol-3-yl)ethylamine;

N,N-dimethyl 2-(5-methoxy-1-methylsulphonyl-1H-indol-3-yl)ethylamine;

[3-(2-dimethylamino-ethyl)-5-hydroxy-1H-indol-1-yl] phenylmethanone;

3-(2-dimethylamino-ethyl)-5-hydroxy-1H-indole-1-carboxylic acid tert-butyl ester;

N,N-dimethyl 2-(1-benzenesulphonyl-5-benzyloxy-1H-indol-3-yl)ethylamine;

N,N-dimethyl 2-(1-benzenesulphonyl-5-hydroxy-1H-indol-3-yl)ethylamine; and

N,N-dimethyl 2-(1-benzenesulphonyl-5-cyano-1H-indol-3-yl)ethylamine.

A further sub-class of compounds in accordance with Formula II is defined by Formula II(b):

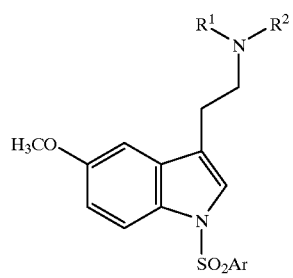

(II(b))

where $R^1$ and $R^2$ have the same meanings as before, and Ar represents an aryl group.

Specific examples of compounds in accordance with Formula II(b) include:

2-[1-(benzenesulphonyl)-5-methoxy-1H-indol-3-yl] ethylamine;

1-benzenesulphonyl-5-methoxy-3-[(2-pyrrolidin-1-yl) ethyl]-1H-indole;

1-benzenesulphonyl-5-methoxy-3-[(2-piperidin-1-yl)ethyl]-1H-indole; and 1-benzenesulphonyl-5-methoxy-3-[(2-piperazin-1-yl) ethyl]-1H-indole.

A third sub-class of compounds in accordance with Formula II is defined by Formula II(c):

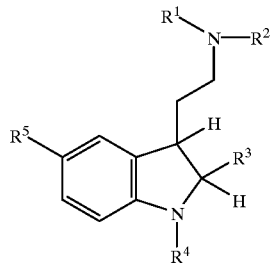

(II(c))

where $R^1$–$R^5$ have the same meanings as before.

Specific examples of compounds in accordance with Formula II(c) include:

N,N-dimethyl 2-(1-benzenesulphonyl-5-methoxy-2,3-dihydro-1H-indol-3-yl)ethylamine.

In the compounds of Formula III, $R^1$ and $R^2$ are preferably identical and represent hydrogen or methyl; $R^3$ preferably represents hydrogen; $R^4$ preferably represents arylsulphonyl, especially p-toluenesulphonyl; $R^6$ preferably represents hydroxy or methoxy; and p is preferably zero. Specific examples of compounds in accordance with Formula III include:

trans-4-dimethylamino-1-(4-methylbenzenesulphonyl)-1,3,4,5-tetrahydrohenz[cd]indol-5-ol; and 4-dimethylamino-5-methoxy-1-(4-methylbenzenesulphonyl)-1,3,4,5-tetrahydro-benz[cd] indole.

The invention also provides or uses pharmaceutical compositions comprising one or more compounds of Formulae I–III in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the pharmaceutical composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to e( delayed in release. A variety of materials can be used for such enteric layers or coatings, such materials including a number of polymeric acids and mixtures of polymeric acids with such materials as shellac, cetyl alcohol and cellulose acetate.

The liquid forms in which the pharmaceutical compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of the relevint clinical conditions, such as depression, Alzheimer's disease, Parkinson's disease and schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

A representative approach to the preparation of compounds of Formula I in which n=1 is illustrated in the following reaction scheme, in which the starting material (methyl indole-4-carboxylate) is prepared as described in J. Org. Chem., 1980, 45, 3350.

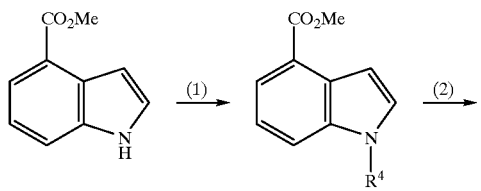

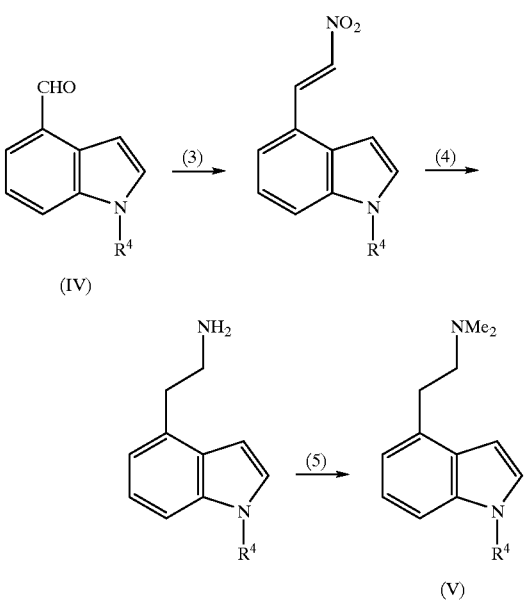

In step (1), reaction of the indole derivative with $R^4Cl$ in the presence of base introduces the desired $R^4$-substituent in the 1-position (where $R^4$ has the same definition as before). Alternatively, and in particular when $R^4$ represents tert-alkoxycarbonyl, this step may be carried out last. In step (2), the methyl ester is first reduced to the corresponding hydroxymethyl derivative, e.g. by means of diusobutyl aluminium hydride, then oxidised to the aldehyde IV using manganese (IV) oxide. In step (3), base-catalysed condensation of the aldehyde with nitromethane affords the 2-nitroethenyl derivative, which may be reduced (e.g. by zinc amalgam) to the 2-aminoethyl derivative (step (4)). If desired, mono- or dialkylation of the primary amino group may be carried out by standard methods. The preferred dimethylamino derivatives (V) are most conveniently prepared by reductive alkylation of the primary amino with formaldehyde in the presence of sodium cyanoborohydride (step (5)).

The above-described indole-4-carboxaldehyde derivatives (IV) are suitable starting materials for the preparation of compounds of Formula I in which n=2, as shown in the following reaction scheme; where $R^1$, $R^2$ and $R^4$ have the same meanings as before:

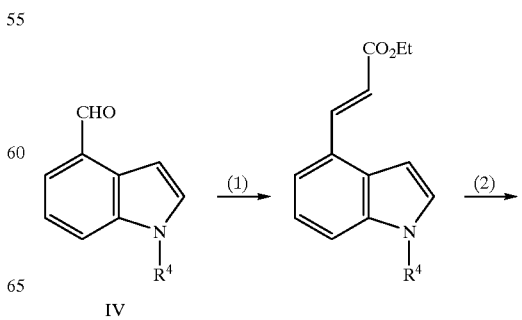

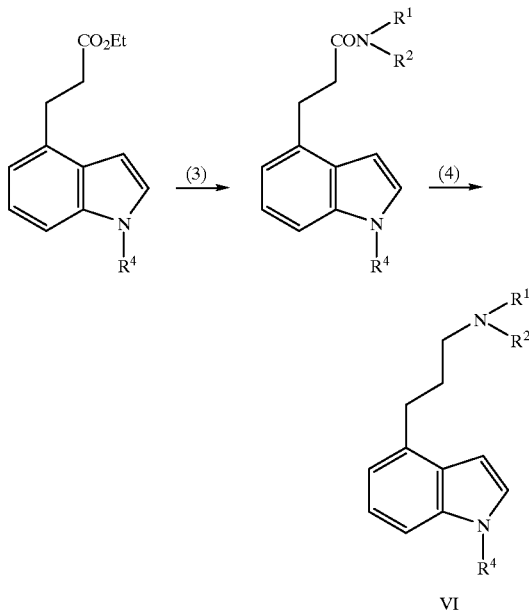

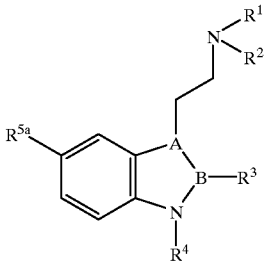

where R[1], R[2], R[3] and R[4] have the same meanings as before, and R[5a] represents any group represented by R[5] except hydroxy.

In the event that either or both of R[1] and R[2] represents hydrogen, it is necessary to protect the exocyclic amino group as the t-butoxycarbonyl (Boc) derivative prior to functionalising the ring nitrogen, the Boc group is being subsequently cleaved under acid conditions.

Compounds of Formula II in which R[5] represents hydroxy may be prepared by hydrogenolysis of the corresponding compounds in which R[5] represents benzyloxy.

In step (1), reaction between the aldehyde (IU) and (carbethoxymethylene) triphenyl phosphorane provides the ethyl ester of the acrylic acid derivative, which is subsequently reduced by catalytic hydrogenation over Pd/C to the corresponding proplonic ethyl ester in step (2). In step (3), reaction of the ester with R[1]R[2] NH provides the corresponding amide, which is then reduced to the amino (VI) by lithium aluminium hydride (step (4)). Alternatively, the same sequence of reactions may be performed on the corresponding N-unsubstituted indoles, with attachment of the R[4] group via reaction with R[4]—Cl as a final step. This is preferable when R[4] represents alkylcarbonyl, tert-alkoxycarbonyl, arylcarbonyl, or heteroarylcarbonyl.

Compounds of Formula I in which R[3] represents alkyl, aryl or arylalkyl may be prepared by the routes shown above, but starting from the appropriate 2-substituted analogue of methyl indole-4-carboxylate.

Compounds of Formula II in which R[5] is other than OH may be prepared from the intermediates VII(a) and VII(b) as shown in the following reaction scheme:

The intermediates VII(b) in which -A-B- represents —CH—CH— may be prepared by catalytic hydrogenation of the intermediates VII(a) in which -A-B- represents —C=C—. Thus, the compounds VII(a):

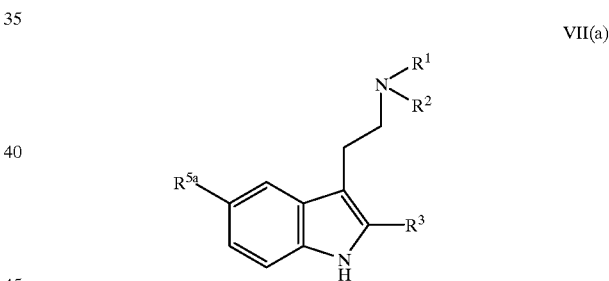

where R[1], R[2], R[5 a] and R[3] have the same meanings as before, are key intermediates in the preparation of compounds of Formula II.

The compound of Formula VII(a) in which R[1] and R[2] represent methyl, R[5a]), represents methoxy, and R[3] represents hydrogen is 5-methoxy-N,N-dimethyltryptamine, available commercially from Sigma, and is the preferred starting material for many of the compounds of Formula II.

Other compounds in accordance with Formula VII(a) may be prepared by a variety of routes, such as:

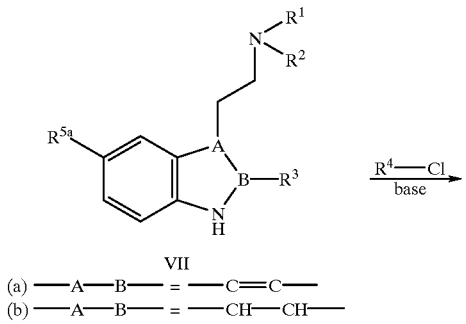

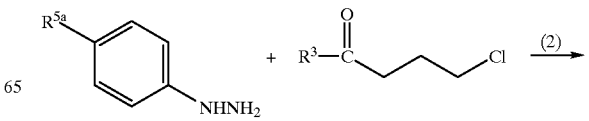

-continued

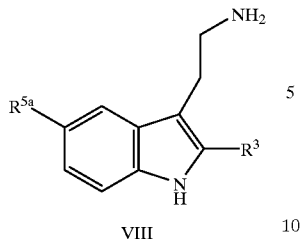

VIII where $R^{5a}$ and $R^3$ have the same meanings as before. The reaction involves the well-known Fischer-indole cyclisation, with in situ substitution of the chlorine by amino (see J. Med. Chem., 1994, 37, 3023). If required, the primary amino group of VIII may be reductively alkylated by reaction with formaldehyde in the presence of sodium cyanoborohydride to provide the compounds VII(a) in which $R^1=R^2=$methyl.

An alternative route to the compounds VIII is depicted in the following reaction scheme:

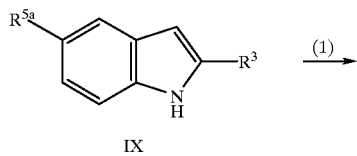

IX

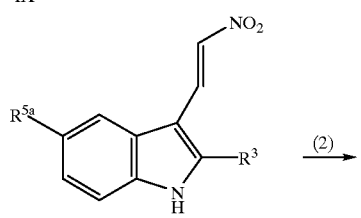

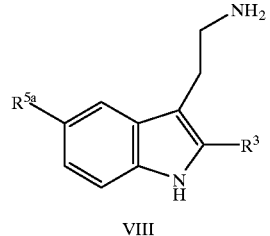

VIII where $R^{5a}$ and $R^3$ have the same meanings as before. Step (1) involves coupling of the indole IX with 1-dimethylamino-2-nitroethylene in the presence of trifluoroacetic acid, and step (2) involves reduction with lithium aluminium hydride. Both steps are described in J. Med. Chem., 1993, 36, 4069.

A further route to the compounds VII(a), also starting from the indoles IX, is depicted in the following reaction scheme:

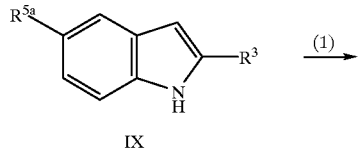

IX

-continued

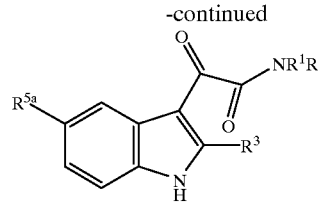

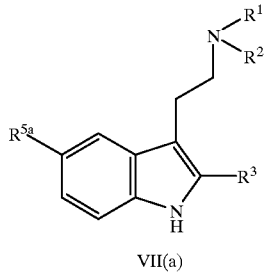

VII(a)

where $R^1$, $R^2$, $R^3$ and $R^{5a}$ have the same meanings as before. Step (1) involves reaction of the indoles IX with oxalyl chloride, followed by condensation with an amine $R^1R^2NH$. Step (2) involves reduction by lithium aluminium hydride of the α-ketoamide group.

The indoles IX may be prepared by the standard Fischer-indole synthesis, or more conveniently (when $R^3$ does not represent hydrogen) by treatment of the N-acyl derivatives X with n-butyllithium:

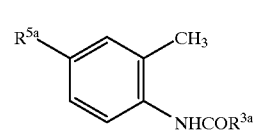

where $R^{5a}$ is defined as before and $R^{3a}$ represents any group represented by $R^3$ except hydrogen (see J. Med. Chem., 1993, 36, 4069).

A preferred route to the compounds of Formula II(b) is shown in the following reaction scheme, in which $R^1$, $R^2$ and Ar have the same meanings as before, and the starting material (5-methoxytryptophol) is commercially available from Sigma.

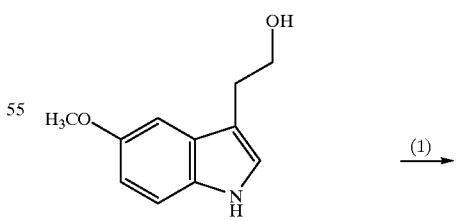

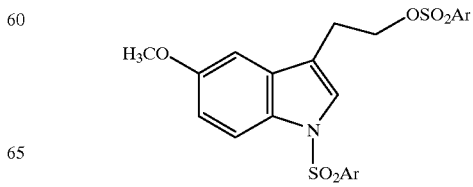

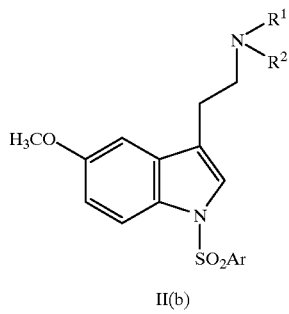

II(b)

Step (1) involves reaction of 5-methoxytryptophol with at least two equivalents of arylsulphonyl chloride in the presence of base. Step (2) involves reaction of the resulting arylsulphonate ester with $R^1R^2NH$ so as to cause nucleophilic displacement of the arylsulphonate group.

Representative compounds of Formula III may be prepared by the route shown in the following reaction scheme, in which $R^4$ has the same meaning as before, and the ketone XI is prepared as described in J. Chem. Soc. Perkin Trans. I, 1972, 1121:

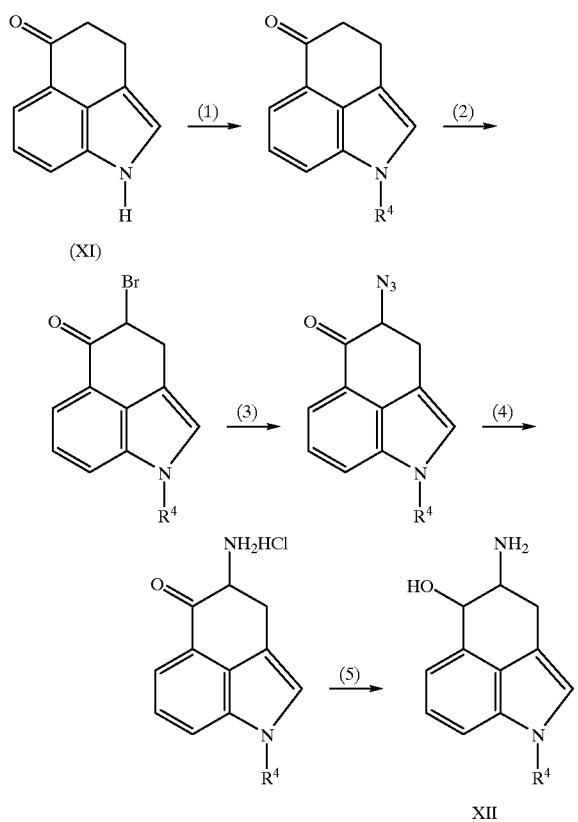

In step (1), reaction of XI with $R^4$—Cl in the presence of base affords the N-substituted derivative, which is then converted (step (2)) to the α-bromoketone by treatment with phenyl trimethyl ammonium bromide perbromide. Nucleophilic displacement of the bromine atom is effected by reaction with sodium azide in DMF (step (3)), and catalytic hydrogenation of the azide over Pd/C (step (4)) affords the corresponding α-aminoketone. Finally, the ketone is reduced by reaction with sodium borohydride (step (5)) to provide the aminoalcohol XII is a racemic mixture. If necessary, the primary amino group of XII may be reductively alkylated (e.g. by hydrogenation over Pd/C in the presence of formaldehyde, acetaldehyde etc.) to form the corresponding N,N-dialkyl derivatives. Additionally, or alternatively, the hydroxyl group of XII may be alkylated by the standard methods of ether synthesis.

It will be understood that any compound of Formula I, II or III initially obtained from any of the above processes may, where appropriate, subsequently be elaborated into a further compound of Formula I, II or III respectively by techniques known from the art. For examples a compound of Formula I, II or III in which $R^3$ represents hydrogen may be reacted with tert-butyllithium to provide the 2-lithio derivative, which may then be reacted with an alkyl, aryl or heteroaryl aldehyde to form a secondary alcohol, which in turn may be oxidised using manganese IV oxide to give the compounds of Formula I, II or III in which $R^3$ represents alkylcarbonyl, arylcarbonyl or heteroarylcarbonyl. Alternatively, the aforementioned secondary alcohols formed by the reaction of the lithio derivative with an alkyl aldehyde may be subjected to dehydrative elimination to form compounds of Formula I, II or III in which $R^3$ represents alkenyl. Furthermore, compounds of Formula I, II or III in which either or both of $R^1$ and $R^2$ represents hydrogen may be alkylated by any of the standard techniques of N-alkylation to provide the corresponding compounds of Formulae I–III in which either or both of $R^1$ and $R^2$ represents alkyl. Suitable techniques of N-alkylation include treatment with the appropriate aldehyde or ketone in the presence of sodium cyanoborohydride. Additionally, a compound of Formula I, II or III in which $R^5$ represents benzyloxy may be converted by catalytic hydrogenation to the corresponding compound of Formula I, II or III in which $R^5$ represents hydroxy, which in turn may be alkylated by standard methods to provide a corresponding compound in which $R^5$ represents alkoxy.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups. such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

2-[1-(Benzenesulphonyl)-1H-indol-4-yl]ethylamine Hydrogen Oxalate a) Methyl 1-( benzenesulphonyl)-1H-indole-4-carboxylate A mixture of methyl indole-4-carboxylate (*J. Org. Chem.* 1980, 45, 3350) (5.0 g, 28.5 mmol), benzenesulphonyl chloride (10.1 g, 57.1 mmol) and anhydrous potassium carbonate (15.78 g, 114 mmol) in butan-3-one (150 ml) was refluxed under nitrogen for 15 hours. Additional benzenesulphonyl chloride (10.1 g) and anhydrous potassium carbonate (10.1 g) were added and refluxing was continued for 5 hours. The mixture was diluted with water (300 ml) and extracted with diethyl ether (3×300 ml). The combined organic solutions were dried (MgSO$_4$) and concentrated to give a white solid which was recrystallised from ethanol (6.35 g, 72%); $\delta_H$ (360 MHz, CDCl$_3$), 8.21 (1H, d, J=8.3 Hz, Ar—H), 7.96 (1H, dd, J=8.1 and 0.7 Hz, Ar—H), 7.87–7.84 (2H, m, Ar—H), 7.69 (1H, d, J=3.7 Hz, Ar—H), 7.56–7.33 (5H, m, Ar—H), 3.94 (3H, s, —OMe); m/z (CI) 316 (M$^+$+1).

b) 1-(Benzenesulphonyl)-1H-indole-4-carboxaldehyde

To a cooled (−70° C.) and stirred solution of methyl 1-(benzenesulphonyl)-1H-indole-4-carboxylate (4.5 g, 14.3 mmol) in anhydrous diethyl ether (50 ml) was added diisobutylaluminium hydride (1M in toluene; 37 ml) over 30 minutes, under a nitrogen atmosphere. After being stirred at −70° C. for 3 hours, excess diisobutylaluminium hydride was destroyed by dropwise addition of methanol (3 ml) and the mixture was allowed to warm to room temperature. 5% Aqueous citric acid (100 ml) was added, products were extracted with ethyl acetate (3×100 ml) and the organic phases were dried (MgSO$_4$) and concentrated. Flash chromatography of the residue (silica gel, hexane-ethyl acetate, 50:50) gave 2.6 g (63%) of the intermediate 1-(benzenesulphonyl)-1H-indole-4-methanol as a thick colourless oil.

To a solution of the above alcohol (2.5 g) in anhydrous dichloromethane (200 ml) was added activated manganese (IV) oxide (9 g) and the resulting mixture was stirred for 15 hours at room temperature, under a nitrogen atmosphere. The manganese residues were removed by filtration, washed with chloroform and the filtrate was concentrated under vacuum to give 1.96 g (79%) of the title compound as a white solid; $\delta_H$ (250 MHz, CDCl$_3$) 7.42–7.56 (5H, m), 7.72 −7.77 (2H, m), 7.86–7.90 (2H, m), 8.28 (1H, d, J=8.25 Hz); 10.18 (1H, s); m/z (EI) 285 (M$^+$). (Found: m/z 285.0444. C$_{15}$H$_{11}$NO$_3$S requires: m/z 285.0460).

c) 1-(Benzenesulphonyl)-4-(2-nitrovinyl)-1H-indole

To a solution of 1- benzenesulphonyl-1H-indole-4-carboxaldehyde (1.9 g, 6.6 mmol) in nitromethane (12 ml) was added ammonium acetate (205 mg, 2.7 mmol) and the resulting mixture was refluxed for 2 hours. Water (50 ml) was added and products were extracted with ethyl acetate (2×100 ml). The combined organic phases were washed with brine (1×30 ml), dried (MgSO$_4$) and concentrated. Flash chromatography (silica gel, dichloromethane-hexane, 75:25) of the residue gave 1.95 g (90%) of the title compound as a pale yellow solid; $\delta_H$ (250 MHz, CDCl$_3$) 8.27 (1H, d, J=13.7 Hz), 8.14 (1H, d, J=8.2 Hz), 7.92–7.87 (2H, m), 7.75 (1H, d, J=3.7 Hz), 7.65 (1H, d, J=13.7 Hz), 7.62–7.34 (5H, m), 6.89 (1H, dd, J=3.7 and 0.9 Hz); m/z (CI) 299 (M$^+$+1).

d) 2-[1-(Benzenesulphonyl)-1H-indol-4-yl]ethylamine Hydrogen Oxalate

Zinc amalgam was prepared by mixing zinc dust (6 g) and mercury (II) chloride (600 mg) in a mixture of water (6 ml) and concentrated hydrochloric acid (300 μl) and stirring at room temperature for 10 minutes. The aqueous phase was decanted off and the amalgam was then covered with methanol.

To a cooled (0° C.) and stirred solution of 1-(benzenesulphonyl)-4-(2nitrovinyl)-1H-indole (1.9 g) in a mixture of methanol (35 ml) and concentrated hydrochloric acid (20 ml) was added portionwise, over 30 minutes, the zinc amalgam prepared above. The mixture was stirred at 0° C. for a further 30 minutes and at room temperature for 2 hours before the solvent was decanted off and evaporated under vacuum. The remaining residue was partitioned between 1M aqueous ammonia (50 ml) and diethyl ether (75 ml) and the aqueous phase was re-extracted with diethyl ether (2×75 ml). The combined ethereal solutions were dried (Na$_2$SO$_4$) and concentrated. Flash chromatography of the residue (silica gel, dichloromethane-methanol-ammonia, 40:8:1) gave 950 mg of the title compound free base as a thick colourless oil; $\delta_H$ (250 MHZ, CDCl$_3$), 7.86 (3H, d), 7.60–7.36 (4H, m), 7.20 (1H, t), 7.04 (1H, d), 6.78 (1H, d), 3.06 (4H, s); m/z (EI) 301 (M$^+$+1).

EXAMPLE 2

N,N-Dimethyl 2-[1-( benzenesulphonyl)-1H-indol-4-yl]ethylamine Hydrogen oxalate

A solution of aqueous formaldehyde (38% w/v; 790 μl) in methanol (10 ml) was added dropwise to a cooled (0° C.) and stirred mixture of 2-[1-(benzenesulphonyl)-1H-indol-4-yl]ethylamine (750 mg), sodium cyanoborohydride (345 mg) and glacial acetic acid (715 μl) in methanol (30 ml). The mixture was then allowed to warm to room temperature and it was stirred for 1 hour before saturated aqueous potassium carbonate (20 ml) was added and the methanol was removed under vacuum. The remaining residue was diluted with water (20 ml) and products were extracted with ethyl acetate (3×50 ml). The combined organic solutions were washed with brine (1×30 ml), (tried (MgSO$_4$) and concentrated. Flash chromatography of the residue (silica gel, dichloromethane-methanol, 90:10) gave 550 mg (67%) of the title compound as a colourless thick oil. The oxalate salt was prepared and recrystallised from isopropanol-ether; mp 192°–195° C.; $\delta_H$ (360 MHz, D$_2$O) 7.93–7.89 (3H, m), 7.77 (1H, d, J=3.6 Hz), 7.60 (1H, t, J=7.6 Hz), 7.50–7.45 (2H, m), 7.35 (1H, t, J=8.2 Hz), 7.19 (1H, d, J=7.5 Hz), 6.91 (1H, d, J=3.9 Hz), 3.43–3.37 (2H, m), 3.28–3.22 (2H, m), 2.89 (6H, s); m/z (EI) 329 (M$^+$+1). (Found: C, 56.73; H, 5.26; N, 6.65. C$_{18}$H$_{20}$N$_2$O$_2$S.1.0 C$_2$H$_2$O$_4$.0.2H$_2$O requires: C, 56.91; H, 5.35; N, 6.64%). (Found: m/z 328.1259. C$_{18}$H$_{20}$N$_2$O$_2$S requires: m/z 328.1246).

EXAMPLE 3

N,N-Dimethyl 2-[1-(dimethylamino)sulphonyl-1H-indol-4-yl]ethylamine. Hydrogen Oxalate The title compound was prepared from 4-[2-(dimethylamino)ethyl]-1H-indole (P. E. Persons et al., *Eur. J. Med. Chem.*, 1991, 26, 473–475) and N,N-dimethylaminosulphonyl chloride following a similar method to that described for Example 6. The oxalate salt was prepared from ethanol-diethyl ether; mp 153°–155° C.; $\delta_H$ (360 MHz, DMSO-d$_6$) 7.78 (1H, d, J=8.6 Hz), 7.70 (1H, d, J=3.6 Hz), 7.30 (1H, t, J=7.6 Hz ), 7.15 (1H, d, J=7.3 Hz), 6.98 (1H, d, J=3.6 Hz), 3.23 (4H, s), 2.80 (6H, s), 2.79 (6H, s); m/z (EI) 296 (M$^+$+1). (Found: C, 49.60; H, 5.89; N, 10.35. C$_{14}$H$_{21}$N$_3$O$_2$S.1.1 C$_2$H$_2$O$_4$ requires: C, 49.33; H, 5.93; N 10.65%).

EXAMPLE 4

N,N-Dimethyl 3-[1-( benzenesulphonyl)-1H-indol-4-yl]propylamine. Hydrogen Oxalate a) 3-[1-(Benzenesulphonyl)-1H-indol-4-yl]acrylic acid ethyl ester A solution of 1-(benzenesulphonyl)-1H-indole-4-carboxaldehyde (2.0 g, 7 mmol) and (carbethoxymethylene)triphenylphosphorane (2.69 g, 7.7 mmol) in anhydrous dichloromethane (50 ml) was heated to reflux for 3 h under a nitrogen atmosphere. The reaction was concentrated and purified by dry flash chromatography (dichloromethane) to give the title compound as a colourless solid (2.49 g, 100%). $\delta_H$ (360 MHZ, CDCl$_3$), 1.34 (3H, t, J=7.2 Hz), 4.27 (2H, q, J=7.2 Hz), 6.51 (1H, d, J=17.2 Hz), 6.94 (1H, d, J=0.72 Hz), 7.32 (1H, t, J=7.9 Hz), 7.43–7.67 (4H, m), 7.67 (1H, d, J=3.6 Hz), 7.68–7.89 (2H, m), 7.94–8.03 (2H, m).

b) 3-[1-(Benzenesulphonyl)-1H-indol-4-yl]propionic acid ethyl ester

3-[1-(Benzenesulphonyl)-1H-indol-4-yl]acrylic acid ethyl ester (2.48 g, 6.98 mmol) was hydrogenated over 10% Pd-C (500 mg) in ethyl acetate-ethanol (4:1; 75 ml), under an atmosphere of hydrogen. The catalyst was removed by filtration after 4 h, and the solvents were removed to obtain the title compound as a colourless oil which crystallised on standing (2.47 g, 100%); $\delta_H$ (CDCl$_3$, 360 MHZ) 1.10 (3H, t, J=6.8 Hz), 2.57 (2H, t, J=7.5 Hz), 3.06 (2H, t, J=7.5 Hz), 4.02 (2H, q, J=7.2 Hz), 6.66 (1H, d, J=0.72 Hz), 6.98 (1H, d, J=7.5 Hz), 7.14–7.18 (1H, m), 7.34–7.38 (2H, m), 7.43–7.48 (1H, m), 7.50 (1H, d, J=3.9 Hz), 7.77–7.82 (3H, m).

c) N,N-Dimethyl-3-[1-( benzenesulphonyl)-1H-indol-4-yl]propionamide

Trimethylaluminium (1.4 ml, 2M solution in hexanes) was added to a suspension of dimethylamine hydrochloride (228 mg, 2.8 mmol) in 10 ml benzene. The reaction was allowed to stir for 1 h before dropwise addition of a solution of 3-[1-(benzenesulphonyl)-1H-indol-4-yl]propionic acid ethyl ester (0.5 g, 1.4 mmol) in benzene (10 ml). The reaction was heated at reflux for 18 h, allowed to cool and then quenched by addition of HCl (2N, 5 ml). The reaction was partitioned between H$_2$O-EtOAc. The organic phase was washed with brine, dried (MgSO$_4$), and concentrated to give the title compound as an oil which crystallised (527 mg, 100%); $\delta_H$ (CDCl$_3$, 250 MHz), 2.63 (2H, t, J=7.5 Hz), 2.79 (2H, br s), 3.16 (2H, t, J=8.5 Hz), 6.74 (1H, d, J=0.7 Hz), 6.08 (1H, d, J=7.5 Hz), 7.21–7.27 (1H, m), 7.41–7.58 (4H, m), 7.84–7.90 (3H, m).

d) N,N-Dimethyl 3-[1-(benzenesulphonyl)-1H-indol-4-yl] propylamine Hydrogen Oxalate A solution of the product from above (527 mg, 1.4 mmol) in 15 ml THF was treated dropwise with lithium aluminium hydride (1.4 ml, 1.0M THF) whilst stirring under a nitrogen atmosphere. The reaction was stirred for 5 h, and quenched with water (1 ml). The reaction was filtered through a glass fibre pad, and the filtrate concentrated. The residue was partitioned between 2N NaOH-EtOAc. The organic phase was dried (Na$_2$SO$_4$), concentrated and purified by chromatography [CH$_2$Cl$_2$-MeOH-NH$_4$OH (95:5:0.5)] to give the title compound free base as an oil (2.75 mg, 50%). The oxalate salt was prepared in diethyl ether; mp 142°–144° C. (Found: C, 56.29; H, 5.06; N, 6.12. C$_{19}$H$_{20}$N$_2$O$_3$S. 1.3 C$_2$H$_2$O$_4$ requires C, 56.46; H, 5.40; N, 6.10). $\delta_H$ (d$_6$-DMSO, 250 MHz) 1.8–2.0 (2H, m), 2.67 (6H, s), 2.78–2.84 (2H, m), 2.98–3.04 (2H, m), 6.97 (1H, d, J=3.75 Hz), 7.11 (1H, d, J=7 Hz), 7.29 (1H, t, J=7.5 Hz), 7.11 (1H, d, J=7 Hz), 7.29 (1H, t, J=7.5 Hz), 7.57–7.73 (3H, m), 7.79–7.85 (2H, m), 7.98–9.01 (2H, m); m/z (ES$^+$) 343 (M$^+$+1).

EXAMPLE 5

N,N-Dimethyl 2-[1-(benzenesulphonyl)-2-benzoyl-1H-indol-4yl]ethylamine. Hydrogen oxalate To a cooled (−78° C.) and stirred solution of N,N-dimethyl 2-[1-(benzenesulphonyl)-1H-indol-4-yl] ethylamine (1.16 g, 3.6 mmol) in anhydrous tetrahydrofuran (8 ml) was added dropwise, under nitrogen, tert-butyllithium (1.7M in pentane, 25 ml). The resulting solution was stirred at −78° C. for 30 minutes and then it was allowed to wirm to 0° C. over 1 h. After being re-cooled to −78° C., a solution of freshly distilled benzaldehyde (415 mg, 3.9 mmol) in anhydrous tetrahydrofuran (4 ml) was added and the mixture was allowed to warm to room temperature over 3 h. The reaction was quenched by addition of water (20 ml) and products were extracted with ethyl acetate (2×75 ml), dried (MgSO$_4$) and concentrated. Flash chromatography (silica gel, dichloromethane-ethanol, 90:10 to dichloromethane-methanol-ammonia, 60:8:1) of the residue gave 600 mg of [1-( benzenesulphonyl)-4-[2-(dimethylamino)ethyl]-1H-indol-2-yl]phenylmethanol as a white solid.

To a solution of the above alcohol (350 mg) in anhydrous dichloromethane (20 ml) was added activated manganese (IV) oxide (250 mg) and the resulting mixture was stirred vigorously at room temperature for 30 minutes. The manganese residues were filtered off, washed with dichloromethane and the filtrate was concentrated under vacuum. Flash chromatography of the residual oil (silica gel, dichloromethane-ethanol, 90:10 to dichloromethane-methanol-ammonia, 60:8:1) gave 330 mg of the title compound as a yellow oil. The hydrogen oxalate salt was prepared and recrystallised from isopropanot-diethyl ether; mp 154°–156° C.; 611 (360 MHz, d$_6$-DMSO) 8.03–7.93 (5H, m), 7.78–7.72 (2H, m), 7.68–7.59 (4H, m), 7.51–7.46 (2H, m), 7.26 (1H, d, J=7.4 Hz), 3.16 (4H, s, —CH$_2$CH$_2$—), 2.73 (6H, s, —NMe$_2$). (Found: C, 61.70; H, 5.07; N, 5.33. C$_{25}$H$_{24}$N$_2$O$_3$S.1.0 C$_2$H$_2$O$_4$..0.2 H$_2$O requires: C, 61.66; H. 5.02; N, 5.33%).

EXAMPLE 6

N,N-Dimethyl 2-[1-(benzenesulphonyl)-5-methoxy-1H-indol-3-yl]ethylamine Hydrochloride To a stirred two-phase mixture of 5-methoxy-N,N-dimethyltryptamine (2 g, 9.16 mmol) and tetrabutylammonium hydrogen sulphate (311 mg, 0.916 mmol) in dichloromethane (120 ml) and 50% aqueous sodium hydroxide (30 ml) was added benzenestull)honyl chloride (2.43 g, 13.74 mmol) over 30 minutes. The mixture was stirred at room temperature for 20 minutes, diluted with ethyl acetate (250 ml) and water (125 ml), and the organic phase was decanted off, washed with brine (2×65 ml), dried (MgSO$_4$) and concentrated. Flash chromatography (silica gel, dichloromethane-methanol-amminia, 95:5:0.5) of the residue afforded 3.166 g (96%) of the title compound free base as a thick oil which solidified on standing. The hydrogen chloride salt was prepared; mp 200–215° C. (EtOH); $\delta_H$ (360 MHz, DMSO-d$_6$) 10.82 (1H, br s), 7.92 (2H, dd, J=8.6 and 1.3 Hz), 7.82 (1H, d, J=9.0 Hz), 7.72–7.65 (2H, m), 7.58 (2H, t, J=7.5 Hz), 7.26 (1H, d, J=2.5 Hz), 6.98 (1H, dd, J=9.0 and 2.5 Hz), 3.80 (3H, s), 3.36–3.28 (2H, m), 3.16–3.28 (2H, m), 3.16–3.06 (2H, m), 2.81 (6H, s); m/z (ES) 359 (M$^+$+1). (Found: C, 58.04; H, 5.97; N, 7.37. C$_{19}$H$_{22}$N$_2$SO$_3$.HCl requires: C, 57.79; H, 5.87; N, 7.09%).

EXAMPLE 7

N,N-Dimethyl 2-[5-methoxy-1-(4-methyl benzenesulphonyl)-1H-indol-3-yl]ethylamine Hydrochloride Following a similar procedure to that described in Example 6, but using p-toluenesulphonyl chloride instead of benzenesulphonyl chloride, the title compound was prepared in 72% yield as a white solid; mp 214°–215° C.; $\delta_H$ (360 MHz, $d_6$-DMSO) 2.32 (3H, s), 2.81 (6H, s), 3.08 (2H, m), 3.37 (2H, m), 3.79 (3H, s), 6.97 (1H, dd, J=9.0, 2.5 Hz), 7.23 (1H, d, J=2.4 Hz), 7.37 (2H, d, J=8.1 Hz), 7.67 (1H, s), 7.79 (2H, d, J=8.4 Hz), 7.80 (1H, d, J=9.1 Hz), 10.60 (1H, br s); m/z (ES$^+$) 373 (MH$^+$). Found: C, 57.66; H, 6.12; N, 6.74. $C_{20}H_{24}N_2O_3S \cdot HCl \cdot 0.4H_2O$ requires C, 57.72; H, 6.25; N, 6.73%.

EXAMPLE 8

N,N-Dimethyl 2-[1-(4-chlorobenzenesulphonyl)-5-methoxy-1H-indol-3-yl]ethylamine Hydrochloride Following a similar procedure to that described in Example 6, but using 4-chlorobenzenesulphonyl chloride instead of benzenesulphonyl chloride, the title compound was prepared in 39% yield as a white solid; mp 222°–224° C.; $d_H$ (360 MHz, $d_6$-DMSO) 2.82 (6H, s), 3.09 (2H, m), 3.35 (2H, m), 3.81 (3H, s), 6.99 (1H, dd, J=9.0, 2.5 Hz), 7.27 (1H, d, J=2.4 Hz), 7.67 (2H, d, J=8.8 Hz), 7.70 (1H, s), 7.82 (1H, d, J=9.0 Hz), 7.94 (2H, d, J=8.7 Hz), 10.65 (1H, br s); m/z (ES$^+$) 395/393 (MH$^{30}$ ). Found: C, 52.76; H, 4.93; N, 6.39. $C_{19}H_{21}ClN_2O_3S \cdot HCl \cdot 0.2H_2O$ requires C, 52.71; H, 5.22; N, 6.47%.

EXAMPLE 9

N,N-Dimethyl 2-[1-(3-chloro benzenesulphonyl)-5-methoxy-1H-indol-3-yl]ethylamine Hydrochloride Following a similar procedure to that described in Example 6, but using 3-chloro benzenesulphonyl chloride instead of benzenesulphonyl chloride, the title compound was prepared in 67% yield as a white solid; mp 191°–194° C.; $\delta_H$ (360 MHz, $d_6$-DMSO) 2.81 (6H, s), 3.09 (2H, m), 3.34 (2H, m), 3.80 (3H, s), 7.00 (1H, dd, J=9.0, 2.5 Hz), 7.26 (1H, d, J=2.4 Hz), 7.61 (1H, t, J=8.0 Hz), 7.73 (1H, s), 7.77 (1H, dt), 7.84 (1H, d, J=9.1 Hz), 7.89 (1H, dt), 7.97 (1H, t, J=1.9 Hz), 10.59 (1H, br s); m/z (ES$^+$) 395/393 (MH$^{30}$ ). Found: C, 52.88; H, 5.12; N, 6.62. $C_{19}H_{21}ClN_2O_3S \cdot HCl$ requires C, 53.15; H, 5.16; N, 6.52%.

EXAMPLE 10

N,N-Dimethyl 2-[5-methoxy-1-(2-naphthalenesulphonyl)-1H-indol-3-yl]ethylamine Hydrochloride Following a similar procedure to that described in Example 6, but using 2-naphthalenesulphonyl chloride instead of benzenesulphonyl chloride, the title compound was prepared in 56% yield as a white solid; mp 191°–193° C.; $\delta_H$ (360 MHz, $d_6$-DMSO) 2.81 (6H, s), 3.09 (2H, m), 3.35 (2H, m), 3.78 (3H, s), 6.98 (1H, dd, J=9.0, 2.4 Hz), 7.23 (1H, d, J=2.4 Hz), 7.72 (2H, m), 7.78 (1H, s), 7.81 (1H, dd, J=8.8, 1.9 Hz), 7.90 (1H, d, J=9.1 Hz), 8.01 (1H, d, J=7.7 Hz), 8.08 (1H, d, J=8.8 Hz), 8.21 (1H, d), 8.76 (1H, s), 10.60 (1H, br s); m/z (ES$^+$) 409 (MH$^{30}$ ). Found: C, 62.19; H, 5.51; N, 6.41. $C_{23}H_{24}N_2O_3S \cdot HCl$ requires C, 62.08; H, 5.66; N, 6.30%.

EXAMPLE 11

N,N-Dimethyl 2-[5-methoxy-1-(4-methoxybenzenesulohonyl)-1H-indol-3-yl]ethylamine Hydrochloride Following a similar procedure to that described in Example 6, but using 4-methoxy benzenesulphonyl chloride instead of benzenesulphonyl chloride, the title compound was prepared in 61% yield as a white solid; mp 152°–155° C.; $\delta_H$ (360 MHz, $d_6$-DMSO) 2.82 (6H, s), 3.08 (2H, m), 3.34 (2H, m), 3.80 (3H, s), 3.81 (3H, s), 6.98 (1H, dd, J=9.0, 2.5 Hz), 7.08 (2H, d, J=9.0 Hz), 7.24 (1H, d, J=2.4 Hz), 7.67 (1H, s), 7.81 (1H, d, J=9.0 Hz), 7.86 (2H, d, J=9.1 Hz), 10.55 (1H, br s): m/z (ES$^+$) 389 (MH$^{30}$ ). Found: C, 56.17; H, 5.94; N, 6.63. $C_{20}H_{24}N_2O_4S \cdot HCl$ requires C, 56.53; H, 5.93; N, 6.59%.

EXAMPLE 12

N,N-Dimethyl 2-[1-(2-chlorobenzenesulphonyl)-5-methoxy-1H-indol-3- yl]ethylamine Hydrochloride Following a similar procedure to that described in Example 6, but using 2-chlorobenzenesulphonyl chloride instead of benzenesulphonyl chloride, the title compound was prepared in 43% yield as a white solid; mp 185°–188° C.; $\delta_H$ (360 MHz, $d_6$-DMSO) 2.84 (6H, s), 3.14 (2H, m), 3.37 (2H, m), 3.81 (3H, s), 6.93 (1H, dd, J=9.0, 2.4 Hz), 7.31 (1H, d, J=2.4 Hz), 7.54 (1H, d, J=9.0 Hz), 7.63 (1H, td), 7.68 (1H, dd), 7.74 (1H, td), 7.78 (1H, s), 8.14 (1H, dd, J=7.9, 1.5 Hz), 10.45 (1H, br s); m/z (ES$^+$) 395/393 (MH$^{30}$ ). Found: C, 53.09; H, 5.06; N, 6.47. $C_{19}H_{21}ClN_2O_3S \cdot HCl$ requires C, 53.15; H, 5.16; N, 6.52%.

EXAMPLE 13

N,N-Dimethyl 2-(1-benzoyl-5-methoxy-1H-indol-3-yl)ethylamine Hydrogen Oxalate Following a similar procedure to that described in Example 6, but using benzoyl chloride instead of benzenesulphonyl chloride, the title compound was prepared in 53% yield as a white solid; mp 199°–201° C.; $\delta_H$ (360 MHz, $d_6$-DMSO) 2.78 (6H, s), 3.05 (2H, m), 3.27 (2H, m), 3.86 (3H, s), 7.02 (1H, dd, J=9.0, 2.4 Hz), 7.28 (1H, d, J=2.4 Hz), 7.32 (1H, s), 7.61 (2H, t, J=7.0 Hz), 7.70 (1H, t, J=7.3 Hz), 7.75 (2H, d, J=6.9 Hz), 8.19 (1H, d, J=9.0 Hz); m/z (ES$^+$) 323 (MH$^{30}$ ). Found: C, 63.89; H, 5.80; N, 7.10. $C_{20}H_{22}N_2O_2 \cdot C_2H_2O_4$ requires C, 64.07; H, 5.87; N, 6.79%.

EXAMPLE 14

N,N-Dimethyl 2-[5-methoxy-1-(2-thiophenesulphonyl)-1H-indol-3-yl]ethylamine Hydrogen Oxalate Following a similar procedure to that described in Example 6, but using 2-thiophenesulphonyl chloride instead of benzenesulphonyl chloride, the title compound was prepared in 25% yield as a white solid; mp 215°–220° C.; $\delta_H$ (360 MHz, $d_6$-DMSO) 2.78 (6H, s), 3.03 (2H, m), 3.29 (2H, m), 3.81 (3H, s), 7.16 (1H, m), 7.20 (1H, d, J=2.3 Hz), 7.61 (1H, s), 7.81 (1H, d, J=9.2 Hz), 7.83 (1H, m), 8.01 (1H, dd, J=5.1, 1.3 Hz); m/z (ES$^+$) 365 (MH$^{30}$ ). Found: C, 50.45; H, 4.89; N, 6.27. $C_{17}H_{20}N_2O_3S_2 \cdot C_2H_2O_4$ requires C, 50.21; H, 4.88; N, 6.16%.

EXAMPLE 15

2-[1-(Benzenesulphonyl)-5-methoxy-1H-indol-3-yl]ethylamine Hydrochloride

To a stirred solution of 5-methoxytryptamine (3.5 g, 18.4 mmol) in dichloromethane (100 ml) was added dropwise a solution of di-tert-butyl dicarbonate (4.02 g, 18.4 mmol) in dichloromethane (25 ml) over 5 minutes. The resulting pale brown solution was allowed to stand at room temperature for 25 h before solvents were removed under vacuum to give a thick oil.

To a stirred two-phase mixture of a solution of the above 3-[2-(tert-butyloxycarbonylamino)ethyl]-5-methoxy-1H-indole in dichloromethane (200 ml) and 50% aqueous sodium hydroxide (50 ml) was added tetrabutylammonium hydrogen sulphate (611 mg, 1.8 mmol) and the mixture was stirred for 10 minutes. Benzenesulphonyl chloride (3.52 ml, 27.6 mmol) was added dropwise uia syringe and the mixture was vigorously stirred for 30 minutes. The mixture was diluted with diethyl ether (500 ml), washed with water (100 ml), brine (2×70 ml), dried ($MgSO_4$) and concentrated. Flash chromatography of the residue (silica gel, dichloromethane-diethyl ether, 90:10) followed by trituration with hexane-diethyl ether (10;1; 100 ml) afforded 1-(benzenesulphonyl)-3-[2-(tert-butyloxycarbonylamino) ethyl]-5-methoxy-1H-indole (7.55 g, 95%) as a white solid; $\delta_H$ (360 MHz, $CDCl_3$) 7.88 (1H, d, J=8.8 Hz), 7.84–7.80 (2H, m), 7.54–7.48 (1H, m), 7.45–7.38 (2H, m), 7.32 (1H, s), 6.96–6.90 (2H, m), 4.55 (1H, br s), 3.82 (3H, s), 3.44–3.36 (2H, m), 2.82 (2H, t, J=6.8 Hz), 1.45 (9H, s).

A solution of the above protected tryptamine (2.1 g, in a mixture of dichloromethane and trifluoroacetic acid (1:1; 60 ml) was allowed to stand at room temperature for 3 h. The solvents were removed under vacuum and the residue was azeotroped with toluene-methanol (5:1; 100 ml). The residue was dissolved in 4N sodium hydroxide solution (50 ml) and extracted with ethyl acetate (3×100 ml). The combined organic solutions were washed with brine (1×50 ml), dried ($Na_2SO_4$) and concentrated. The hydrochloride salt was prepared and recrystallised from acetonitrile to give 1.53 g of the title compound; mp 117°–120° C.; $\delta_H$ (360 MHz, $D_2O$) 7.81 (2H, d, J=7.5 Hz), 7.74 (1H, d, J=9.0 Hz), 7.56 (1H, s), 7.54 (1H, t, J=7.5 Hz), 7.41 (2H, t, J=8.1 Hz), 7.00 (1H, d, J=2.3 Hz), 6.89 (1H, dd, J=9.0 and 2.3 Hz), 6.89 (1H, dd, J=9.0 and 2.3 Hz), 3.78 (3H, s),3.29 (2H, t, J=7.6 Hz), 3.01 (2H, t, J=7.6 Hz); m/z (ES) 331 ($M^+$+1). (Found: C, 54.07; H, 5.39; N, 7.41. $C_{17}H_{18}N_2O_3S.1.0HCl.0.6$ $H_2O$ requires: C, 54.06; H, 5.39; N, 7.42%).

EXAMPLE 16

1-Benzenesulphonyl-5-methoxy-3-[(2-pyrrolidin-1-yl)ethyl]-1H-indole Hydrogen Oxalate
a) Benzenesulphonic acid 2-(1-benzenesulphonyl-5-methoxy-1H-indol-3-yl)ethyl ester To a stirred two-phase mixture of 5-methoxytryptophol (0.150 g, 0.785 mmol) and tetrabutylammonium hydrogen sulphate (27 mg, 0.0785 mmol) in 50% aqueous NaOH (3 ml) and dichloromethane (30 ml) was added benzenesulphonyl chloride (0.25 ml, 1.96 mmol) dropwise over 5 min. The mixture was stirred for 20 min, more benzenesulphonyl chloride 0.10 ml, 0.784 mmol) was added dropwise, and the mixture was stirred for a further hour. The organic layer was washed with brine, dried ($Na_2SO_4$) and evaporated in vacuo. The residue was purified by flash chromatography (silica gel, 50–100% EtOAc/hexane) to afford 0.095 g (37%) of 2-(1-benzenesulphonyl-5-methoxy-1H-indol-3-yl)ethanol and 0.191 g (52%) of the title compound; $\delta_H$ (360 MHz, $d_6$-DMSO) 2.98 (2H, t, J 6.1 Hz), 3.71 (3H, s), 4.30 (2H, t, J=6.2 Hz), 6.92 (1H, dd, J=8.9, 2.5 Hz), 6.95 (1H, d, J=2.2 Hz), 7.47 (2H, t, J=7.8 Hz), 7.53–7.59 (3H, m), 7.63–7.67 (4H, m), 7.77 (1H, d, J=8.9 Hz), 7.89 (2H, m); m/z ($ES^+$) 510 $(M+K)^+$, 494 $(M+Na)^+$, 489 $(M+NH_4)^+$, 472 $(M+H)^+$.
b) 1-Benzenesulphonyl-5-methoxy-3-[(2-pyrrolidin-1-yl) ethyl]-1H-indole Hydrogen Oxalate To a stirred solution of benzenesulphonic acid 2-(1-benzenesulphonyl-5-methoxy-1H-indol-3-yl)ethyl ester (0.191 g, 0.405 mmol) in anhydrous 2-propanol (10 ml) under nitrogen was added anhydrous potassium carbonate (0.112 g, 0.810 mmol), then a solution of pyrrolidine (0.17 ml, 2.03 mmol) in anhydrous 2-propanol (3 ml). The mixture was heated at reflux for 4 h, and the solvents were then removed in vacuo. The residue was partitioned between dichloromethane and water, and the aqueous layer was extracted further with dichloromethane. The combined organic extracts were washed with brine (2×25 ml), dried ($Na_2SO_4$), and evaporated in vacuo. The residue was purified by flash chromatography (silica gel, $CH_2Cl_2$—MeOH—$NH_3$; 95:5:0.5) to give 0.102 g (65%) of the title compound free base. The oxalate salt was prepared in EtOH-$Et_2O$ as a white solid; mp 217°–220° C.; $\delta_H$ (360 MHz, $d_6$-DMSO) 1.94 (4H, s), 3.03 (2H, m), 3.27 (4H, s), 3.40 (2H, m), 3.79 (3H, s), 6.98 (1H, dd, J=9.0, 2.3 Hz), 7.17 (1H, d, J=2.3 Hz), 7.58 (2H, t, J=8.0 Hz), 7.69 (2H, m), 7.82 (1H, d, J=9.0 Hz), 7.92 (2H, d, J=7.9 Hz); m/z ($ES^+$) 385 ($MH^{30}$ ). Found: C, 57.83; H, 5.31; N, 5.87. $C_{21}H_{24}N_2O_3S.C_2H_2O_4$ requires C, 58.22; H, 5.52; N, 5.90%.

EXAMPLE 17

1-Benzenesulphonyl-5-methoxy-3-[(2-piperidin-1-yl)ethyl]-1H-indole Hydrogen Oxalate Following a similar procedure to that described in Example 16, step b, but using piperidine instead of pyrrolidine, the title compound was prepared in 90% yield as a white solid; mp 231°–234° C.; $\delta_H$ (360 MHz, $d_6$-DMSO) 1.55 (2H, m), 1.75 (4H, m), 3.04 (2H, m), 3.15 (4H, s), 3.27 (2H, m), 3.79 (3H, s), 6.98 (1H, dd, J=9.0, 2.4 Hz), 7.15 (1H, d, J=2.4 Hz), 7.58 (2H, t, J=8.0 Hz), 7.68 (2H, m), 7.82 (1H, d, J=9.0 Hz), 7.91 (2H, d, J=7.7 Hz); m/z ($ES^+$) 399 ($MH^{30}$ ). Found: C, 58.40; H, 5.91; N, 5.81. $C_{22}H_{26}N_2O_3S.C_2H_2O_4.0.3H_2O$ requires C, 58.36; H, 5.84; N, 5.67%.

EXAMPLE 18

1-Benzenesulphonyl-5-methoxy-3-[(2-piperazin-1-yl)ethyl]-1H-indole Hydrogen Oxalate Following a similar procedure to that described in Example 16, step b, but using piperazine instead of pyrrolidine, the title compound was prepared in 76% yield as a white solid ml) 230°–232° C.; $\delta_H$ (360 MHz, $d_6$-DMSO) 2.70 (3H, s), 2.82 (8H, br, s), 3.09 (4H, br s), 3.78 (3H, s), 6.96 (1H, dd, J=9.0 Hz), 7.08 (1H, d), 7.57 (2H, t, J=7.5 Hz), 7.60 (1H, s), 7.68 (1H, t, J=7.5 Hz), 7.81 (1H, d, J=9.0 Hz), 7.90 (2H, d, J=7.6 Hz); m/z ($ES^+$) 414 ($MH^+$). Found: C, 44.48; H, 4.85; N, 5.13. $C_{22}H_{27}N_3O_3S.4C_2H_2O_4.2H_2$ O requires C, 44.50; H, 4.86; N, 5.19%,.

EXAMPLE 19

N,N-Dimethyl 2-(1-benzenesulphonyl-5-methoxy-2-methyl-1H-indol-3-yl)ethylamine Hydrogen Oxalate
a) N,N-Dimethyl 2-(5-methoxy-2-methyl-1H-indol-3-yl) ethylamine To a stirred solution of 2-(5-methoxy-2-methyl-1H-indol-3-yl)ethylamine hydrochloride (Spadoni, G. et al. *J. Med. Chem.* 1993, 36, 4069–4074) (1.6 g, 6.55 mmol) in methanol (100 ml) was added a 30% w/v solution of sodium methoxide in methanol (1.24 ml, 6.55 mmol), then acetic acid (1.50 ml, 26.2 mmol), followed by sodium cyanoborohydride (0.82 g, 13.1 mmol). A 38% w/v aqueous solution of formaldehyde (1.24 ml, 15.7 mmol) in methanol (30 ml) was then added dropwise over 40 min, and the mixture was stirred overnight before 4N aqueous NaOH (50 ml) was added. The methanol was removed in vacuo and the aqueous residue was extracted with ethyl acetate. The organic extract was washed with brine (50 ml), dried (Na$_2$SO$_4$), and evaporated in vacuo to give 1.215 g (80%) of the title compound; δ$_H$ (360 MHz, CDCl$_3$) 2.35 (3H, s), 2.36 (6H, s), 2.50 (2H, m), 3.85 (2H, m), 3.85 (3H, s), 6.76 (1H, dd, J=8.7, 2.5 Hz), 6.97 (1H, d, J=2.3 Hz), 7.13 (1H, d, J=8.5 Hz), 7.72 (1H, br s).

b) N,N-Dimethyl 2-(1-benzenesulphonyl-5-methoxy-2-methyl-1H-indol-3-yl)ethylamine Hydrogen Oxalate Following a similar procedure to that described in Example 6, but using N,N-dimethyl 2-(5-methoxy-2-methyl-1H-indol-3-yl)ethylamine instead of 5-methoxy-N,N-dimethyltryptamine the title compound was prepared as a white solid; mp 194°–196° C.; δ$_H$ (360 MHz, d$_6$-DMSO) 2.54 (3H, s), 2.76 (6H, s), 2.98 (2H, m), 3.44 (2H, m), 3.80 (3H, s), 6.92 (1H, dd, J=9.0, 2.5 Hz), 7.09 (1H, d, J=2.5 Hz), 7.56 (2H, t, J=7.5 Hz), 7.67 (1H, t, J=7.5 Hz), 7.77 (2H, d, J=7.4 Hz), 7.94 (1H, d, J=9.1 Hz); m/z (ES$^+$) 373 (MH$^+$). Found: C, 56.16; H, 5.52; N, 6.09. C$_{20}$H$_{24}$N$_2$O$_3$S.C$_2$H$_2$O$_4$.0.4H$_2$O requires C, 56.25; H, 5.75; N, 5.96%.

Examples 20, 21 and 22 were prepared from the appropriate tryptamine compounds and the corresponding sulphonyl chloride following similar methods to that described for Example 6.

EXAMPLE 20

N,N-Dimethyl 2-(1-Benzenesulphonyl-1H-indol-3-yl)ethylamine Hydrogen Oxalate mp 196°–198° C. (EtOH-Et$_2$O); δ$_H$ (360 MHz, DMSO-d$_6$) 7.97–7.91 (3H, nm), 7.74 (1H, s), 7.72–7.64 (2H, m), 7.61 (2H, t, J=8.0 Hz), 7.38 (1H, t, J=7.3 Hz), 7.29 (1H, t, J=7.3 Hz), 3.34–3.26 (2H, m), 7.08–3.00 (2H, m), 2.77 (6H, s); m/z (CI) 329 (M$^+$+1). (Found: C, 57.06; 5.40, N, 6.58. C$_{18}$H$_{20}$N$_2$O$_2$S.1.0 C$_2$H$_2$O$_4$ requires: C, 57.40; H, 5.30; N, 6.69%).

EXAMPLE 21

N,N-Dimethyl 2-(1-methylsulphonyl-1H-indol-3-yl) ethylamine Hydrogen Oxalate mp 191°–193° C. (EtOH-Et$_2$O); δ$_H$ (360 MHz, DMSO-d$_6$) 7.83 (1H, d, J=8.1 Hz), 7.75 (1H, d, J=7.3 Hz), 7.52 (1H, s), 7.44–7.30 (2H, m), 3.37 (3H, s), 3.36–3.28 (2H, m), 3.14–3.05 (2H, m), 2.79 (6H, s); m/z (CI) 267 (M$^+$+1). (Found: C, 49.93; H, 5.52; N, 7.76. C$_{13}$H$_{18}$N$_2$O$_2$S.1.1 C$_2$H$_2$O$_4$ requires: C, 49.96; H, 5.57; N, 7.67%).

EXAMPLE 22

N,N-Dimethyl 2-(5-methoxy-1-methylsulphonyl-1H-indol-3-yl)ethylamine. Hydrogen Oxalate mp 201°–203° C. (EtOH-Et$_2$O); δ$_H$ (360 MHz, DMSO-d$_6$) 7.71 (1H, d, J=9.0 Hz), 7.48 (1H, s), 7.25 (1H, d, J=2.4 Hz), 7.01 (1H, dd, J=9.0 and 2.4 Hz), 3.83 (3H, s), 3.36–3.28 (5H, m and s), 3.10–3.02 (2H, m), 2.79 (6H, s); m/z (CI) 297 (M$^+$+1). (Found: C, 49.74; H, 5.56; N, 7.07. C$_{14}$H$_{20}$N$_2$O$_3$S.1.0 C$_2$H$_2$O$_4$ requires: C, 49.73; H, 5.74; N, 7.25%).

EXAMPLE 23

[3-(2-Dimethylamino-ethyl)-5-hydroxy-1H-indol-1-yl]phenylmethanone a) 2-(5-Benzyloxy-1H-indol-3-yl)-N,N-dimethyl-2-oxo-acetamide Oxalyl chloride (3.9 ml, 45 mmol) was added to a stirred solution of 5-benzyloxyindole (5.0 g, 22 mmol) in dry tetrahydrofuran (200 ml), at 0° C. under nitrogen. The cooling bath wvas removed and the reaction was stirred at room temperature for 3 hours. The reaction was then cooled to 0° C. and dimethylamine was bubbled through the solution for 5 minutes (a heavy white precipitate forms). The whole mixture was then poured into 4N hydrochloric acid (50 ml). The layers were separated and the aqueous was extracted with diethylether (×1). The combined organic layers were dried (Na$_2$SO$_4$), filtered and evaporated to give the title compound (6.4 g, 89%) as an off-white solid; δ$_H$ (360 MHz, d$_6$-DMSO) 2.90 (3H, s), 2.98 (3H, s), 5.14 (2H, s), 6.99 (1H, dd, J=8.3 and 2.0 Hz), 7.31–7.50 (6H, m), 7.71 (1H, d, J=2.0 Hz), 8.02 (1H, s), 12.2 (1H, br s).

b) [2-(5-Benzyloxy-1H-indol-3-yl)ethyl]dimethylamine

A solution of lithium aluminium hydride (1.0M, 120 ml, 120 mmol) was added to a stirred solution of 2-(5-benzyloxy-1H-indol-3-yl)-N,N-dimethyl- 2-oxo-acetamide (6.4 g, 19.9 mmol) in dry tetrahydrofuran (100 ml) at room temperature under nitrogen. (Gas evolution and precipitate formation were observed) The reaction was then stirred and heated at reflux for 4 hours. The mixture was then cooled to 0° C., and quenched with water (4.5 ml), 4N sodium hydroxide (4.5 ml). Ethyl acetate and anhydrous sodium sulphate were then added. After stirring at room temperature overnight, the precipitate was removed by filtration (washing with ethyl acetate). The filtrate was evaporated and the residue was purified by chromatography on silica gel, eluting with dichloromethane/methanol/aqueous ammonia (80:8:1) to give the title amine (4.0 g, 68%) as a thick oil which solidifies upon standing; δ$_H$ (360 MHz, CDCl$_3$) 2.33 (6H, s), 2.58–2.62 (2H, m), 2.87–2.91 (2H, m), 5.10 (2H, s), 6.92 (1H, dd, J=8.8 and 2.4 Hz), 6.98 (1H, d, J=2.2 Hz), 7.12 (1H, d, J=2.4 Hz), 7.23–7.48 (6H, m), 8.0 (1H, br s).

c) [5-Benzyloxy-3-(2-dimethylamino-ethyl)-1H-indol-1-yl]phenylmethanone

Benzoyl chloride (217 ml, 1.9 mmol) was added to a stirred solution of [2-(5-benzyloxy-1H-indol-3-yl)ethyl]dimethylamine (500 mg, 1.7 mmol), triethylamine (473 ml, 3.4 mmol) and 4-(dimethylamino)pyridine (20 mg, 0.2 mmol) in dry dichloromethane (5 ml) at 0° C. The reaction was allowed to warm slowly to ambient temperature, and stirred at this temperature overnight. The reaction was quenched with saturated aqueous sodium hydrogen carbonate. The aqueous was then extracted with dichloromethane (×3). The combined extracts were dried (Na$_2$SO$_4$), filtered and evaporated. The residue was purified by chromatography on silica gel, eluting with dichloromethane/methanol/aqueous ammonia (80:8:1) to give the title compound (327 mg, 48%) is a thick oil. δ$_H$ (250 MHz, CDCl$_3$) 2.30 (6H, s), 2.52–2.60 (2H, m), 2.78–2.84 (2H, m), 5.16 (2H, s), 7.06–7.10 (3H, m), 7.30–7.64 (10H, m), 8.28 (0.5H, s), 8.32 (0.5H, s).

d) [3-(2-Dimethylamino-ethyl)-5-hydroxy-1H-indol-1-yl]phenylmethanone

A solution of [5-benzyloxy-3-(2-dimethylamino-ethyl)-1H-indol-1yl]phenylmethanone (300 mg, 0.75 mmol) and 4N hydrochloric acid (190 ml, 0.76 mmol) in ethanol (10 ml) was hydrogenated over 10% palladium on carbon (100 mg) at 35 psi for 3 hours. The catalyst was removed by filtration. The filtrate was evaporated, and the residue was partitioned between dichloromethane and saturated aqueous sodium hydrogen carbonate. The aqueous was further extracted with dichloromethane (×2). The combined extracts were dried (K$_2$CO$_3$), filtered and evaporated. The residue was purified by chromatography on silica gel, eluting with dichloromethane/methanol/aqueotus ammonia (80:8:1) to give the title compound (120 mg, 52%), as a colourless solid; mp 154°–156° C. $\delta_H$ (360 MHz, CDCl$_3$) 2.40 (6H, s), 2.70–2.75 (2H, m), 2.83–2.88 (2H, m), 6.86–6.90 (2H, m), 7.04 (1H, s), 7.49–7.61 (3H, m), 7.68–7.71 (2H, m), 8.17 (0.5H, s), 8.20 (0.5H, s). m/z (CI$^+$) 309 [MH]$^+$. Found: C, 73.22; H, 6.48; N, 8.74. C$_{19}$H$_{20}$N$_2$O$_2$.0.2 H$_2$O requires C, 73.15; H, 6.59; N, 8.98%.

EXAMPLE 24

3-(2-Dimethylamino-ethyl)-5-hydroxy-1H-indole-1-carboxylic acid tert-butyl ester a) 5-Benzyloxy-3-(2-dimethylamino-ethyl)-1H-indole-1-carboxylic acid tert-butyl ester Di-tert-butyl dicarbonate (408 mg, 1.9 mmol) was added to a stirred solution of [2-(5-benzyloxy-1H-indol-3-yl)ethyl] dimethylamine (500 mg, 1.7 mmol), triethylamine (473 ml, 3.4 mmol) and 4-(dimethylamino)-pyridine (20 mg, 0.2 mmol) in dry dichloromethane (5 ml) at 0° C. The reaction was allowed to warm slowly to ambient temperature. After 3 hours the mixture was poured into saturated aqueous sodium hydrogen carbonate and extracted with dichloromethane (×3). The combined extracts were dried (Na$_2$SO$_4$), filtered and evaporated. The residue was purified by chromatography on silica gel, eluting with dichloromethane/methanol/aqueous ammonia (80:8:1) to give the title compound (630 mg, 95%) as a thick oil. $\delta_H$ (360 MHz, CDCl$_3$) 1.65 (9H, s), 2.33 (6H, s), 2.58–2.62 (2H, m), 2.79–2.83 (2H, m), 5.12 (2H, s), 6.99 (1H, dd, J=9.0 and 2.5 Hz), 7.06 (1H, d, J=2.5 Hz), 7.29–7.48 (6H, m), 8.0 (1H, br d).

b) 3-(2-Dimethylamino-ethyl)-5-hydroxy1H-indole-1-carboxylic acid tert-butyl ester A solution of 5-benzyloxy-3-(2-dimethylamino-ethyl)-1H-indole-1-carboxylic acid tert-butyl ester (303 mg, 0.77 mmol) and 4N hydrochloric acid (192 ml, 0.77 mmol) in ethanol (10 ml) was hydrogenated over 10% palladium on carbon (100 mg) at 40 psi for 4 hours. The catalyst was removed by filtration. The filtrate was evaporated and the residue was partitioned between aqueous sodium hydrogen carbonate and dichloromethane. The aqueous was further extracted with dichloromethane (×2). The combined extracts were dried (K$_2$CO$_3$), filtered and evaporated. The residue was purified by chromatography on silica gel, eluting with dichloromethane/methanol/aqueous ammonia (60:8:1) to give the title compound (117 mg, 50%) as a colourless solid. $\delta_H$ (360 MHz, CDCl$_3$) 1.64 (9H, s), 2.45 (6H, s), 2.73–2.80 (2H, m), 2.88–2.93 (2H, m), 6.82–6.85 (1H, m), 6.96 (1H, br s), 7.33 (1H, br s), 7.92 (1H, m). m/z (CI$^+$) 305 [MH]$^+$. Found: C, 64.07; H, 8.07; N, 8.71. C$_{17}$H$_{24}$N$_2$O$_3$. 0.8 H$_2$O requires C, 64.01; H, 8.15; N, 8.78%.

EXAMPLE 25

N,N-Dimethyl 2-(1-Benzenesulphonyl-5-benzyloxy-1H-indol-3-yl)ethylamine Hydrogen Oxalate To a stirred solution of 5-benzyloxytryptamine hydrochloride (2.29 g, 7.56 mmol) in methanol (100 ml) was added sodium methoxide (30% w/v in methanol; 1.44 ml) followed by glacial acetic acid (1.70 ml, 30.2 mmol) and sodium cyanoborohydride (950 mg, 15.12 mmol). A solution of formaldehyde (38% w/v aqueous solution; 1.43 ml) in methanol (25 ml) was then added dropwise over 20 minutes, and the resulting solution was stirred at room temperature for 4 h. 4N Sodium hydroxide (60 ml) was added and the methanol was removed under vacuum. The aqueous residue was extracted with diethyl ether (2×250 ml) and the combined organic phases were washed with brine (2×50 ml), dried (Na$_2$SO$_4$) and concentrated. The residue was dissolved in dichloromethane (120 ml) and 50% aqueous sodium hydroxide (40 ml) was added followed by tetrabutylammonium hydrogen sulphate (258 mg). The mixture was vigorously stirred, benzenesulphonyl chloride (1.45 ml) in dichloromethane (10 ml) was added dropwise over 3 minutes and stirring was continued for 30 minutes. Water (120 ml) and diethyl ether (200 ml) were added and the organic phase was decanted off, washed with brine (2×50 ml), dried (Na$_2$SO$_4$) and concentrated. Flash chromatography of the residue (silica gel, dichloromethane-methanol-ammonia, 95:5:0.5) afforded 2.57 g (78%) of the title compound free base as a colourless thick oil. The oxalate salt was prepared; mp 212°–215° C. (EtOH); $\delta_H$ (360 MHz, DMSO-d$_6$) 7.94–7.90 (2H, m), 7.82 (1H, d, J=9.0 Hz), 7.72–7.64 (2H, m), 7.58 (2H, t, J=8.0 Hz), 7.48–7.28 (6H, m), 7.06 (1H, dd, J=9.0 and 2.4 Hz), 5.12 (2H, s), 3.30–3.22 (2H, m), 3.06–2.98 (2H, m), 2.77 (6H, s); m/z (ES) 435 (M$^+$+1). (Found: C, 61.81; H, 5.38; N, 5.48. C$_{25}$H$_{26}$N$_2$O$_3$S.1.0 C$_2$H$_2$O$_4$ requires: C, 61.82; H, 5.38; N, 5.34%).

EXAMPLE 26

N,N-Dimethyl 2-(1-benzenesulphonyl-5-hydroxy-1H-indol-3-yl)ethylamine

A solution of N,N-dimethyl 2-(1-benzenesulphonyl-5-benzyloxy-1H-indol-3-yl)ethylamine (2.25 g, 4.6 mmol) in absolute ethanol (100 ml) was hydrogenated at 40 psi over 20% palladium hydroxide (600 mg) for 4.5 h. Additional catalyst (1.6 g) was then added and hydrogenation was resumed at 45 psi for 2.5 h. The catalyst was removed by filtration, washed with a mixture of dichloromethane-methanol-ammonia (80:20:2; 3×70 ml), and the filtrate was concentrated under vacuum. The residue was purified by flash chromatography (silica gel, dichloromethane-methanol-ammonia, 95:5:0.5) to give the title compound as a crystalline solid after trituration with diethyl ether (30 ml); mp 185°–188° C.; $\delta_H$ (360 MHz, DMSO-d$_6$) 9.32 (1H, br s), 7.90–7.84 (2H, m), 7.69 (1H, d, J=8.7 Hz), 7.68–7.62 (1H, m), 7.55 (2H, t, J=8.0 Hz), 7.48 (1H, s), 6.82 (1H, d, J=2.2 Hz), 6.78 (1H, dd, H=8.8 and 2.2 Hz), 2.67 (2H, t, J=7.6 Hz), 2.47 (2H, t, J=7.6 Hz), 2.18 (6H, s); m/z (ES) 345 (M$^+$+1). (Found: C, 62.91; H, 5.86; N, 8.16. C$_{18}$H$_{20}$N$_2$O$_3$ requires: C, 62.77; H, 5.85; N, 8.13%).

EXAMPLE 27

N,N-Dimethyl 2-(1-benzenesulphonyl-5-cyano-1H-indol-3-yl)ethylamine Hydrogen Oxalate To a stirred solution of 3-(2-anminoethyl)-5-cyano-1H-indole hydrochloride (Castro, J. L. et al. *J. Med. Chem.* 1994, 37, 3023–3032) (0.1208 g, 0.545 mmol) in methanol (25 ml) was added a 30% w/v solution of sodium methoxide in methanol (0.1 ml, 0.545 mmol), then acetic acid (0.125 ml, 2.18 mmol), followed by sodium cyanoborohydride (68 mg, 1.09 mmol). A 38% w/v aqueous solution of formaldehyde (0.103 ml, 1.31 mmol) in methanol (10 ml) was then added dropwise over 30 min. The mixture was stirred for 3.5 h, then 4N aqueous NaOH (25 ml) was added, and the methanol was removed in vacuo. The aqueous residue was extracted with diethyl ether (3×25 ml), and the combined organic extracts were washed with brine (2×20 ml), dried (Na$_2$SO$_4$), and evaporated in vacuo to give crude N,N-dimethyl 2-(5-cyano-1H-indol-3-yl)ethylamine.

To this crude product was added dichloromethane (30 ml), 50% aqueous NaOH (2 ml), and tetrabutylammonium hydrogen sulphate (19 mg, 0.0545 mmol). Benzenesulphonyl chloride (0.104 ml, 0.817 mmol) was then added dropwise over 3 min whilst stirring magnetically, and the mixture was stirred for 30 min. Ethyl acetate (50 ml) and water (25 ml) was then added, and the organic layer was washed with brine (2×25 ml), dried ($Na_2SO_4$), and evaporated in vacuo. The residue was purified by flash chromatography (silica gel, $CH_2Cl_2$—MeOH—$NH_3$(aq); 95:5:0.5) to yield 0.132 g (66%) of the title compound free base. The oxalate salt was prepared in EtOH-$Et_2$O as a white solid; mp 213°–220° C.; $\delta_H$ (360 MHz, $d_6$DMSO) 2.78 (6H, s), 3.10 (2H, m), 3.31 (2H, m), 7.63 (2H, t, J=7.5 Hz), 7.74 (1H, t, J=7.5 Hz), 7.78 (1H, dd, J=8.6, 1.4 Hz), 7.98 (1H, s), 8.03 (2H, d, J=7.4 Hz), 8.11 (1H, d, J=8.4 Hz), 8.31 (1H, s); m/z ($ES^+$) 354 ($MH^{30}$). Found: C, 57.01; H, 4.83; N, 9.22. $C_{19}H_{19}N_3O_2S \cdot C_2H_2O_4$ requires C, 56.88; H, 4.77; N, 9.48%.

EXAMPLE 28

N,N-Dimethyl 2-(1-benzenesulphonyl-5-methoxy-2,3-dihydro-1H-indol-3-yl)ethylamine Hydrogen Oxalate a) N,N-Dimethyl 2-(5-methoxy-2,3-dihydro-1H-indol-3-yl)ethylamine A mixture of 5-methoxy-N,N-dimethyltryptamine (0.200 g, 0.939 mmol) and palladium on carbon (10%, 200 mg) in 50 M aqueous HCl (50 ml) was hydrogenated at 50 psi overnight. The catalyst was removed by filtration, and the filtrate was extracted with dichloromethane (3×25 ml). The combined organic extracts were evaporated in vacuo and the residue was purified by flash chromatography (silica gel, $CH_2Cl_2$—MeOH—$NH_3$(aq); 92:8:0.8) to give 94 mg (47%) of the title compound; $\delta_H$ (250 MHz, $CDCl_3$) 1.71 (1H, m), 1.99 (1H, m), 2.26 (6H, s), 2.37 (2H, m), 3.20 (1H, t, J=8.0 Hz), 3.27 (1H, m), 3.68 (1H, t, J=8.0 Hz), 3.75 (3H, s), 6.60–6.61 (2H, m), 6.73 (1H, m).

b) N,N-Dimethyl 2-(1-benzenesulphonyl-5-methoxy-2,3-dihydro-1H-indol3-yl)ethylamine Hydrogen Oxalate Following a similar procedure to that described in Example 6, but using N,N-dimethyl 2-(5-methoxy-2,3-dihydro-1H-indol-3-yl)ethylamine instead of 5-methoxy-N,N-dimethyltryptamine, the title compound was prepared in 57% yield as a white solid; mp 183°–185° C.; $\delta_H$ (360 MHz, $d_6$DMSO) 1.47 (1H, m), 1.94 (1H, m), 2.68 (6H, s), 2.96 (2H, m), 3.14 (1H, m), 3.63 (1H, m), 3.71 (3H, s), 4.06 (1H, m), 6.82 (2H, m), 7.42 (1H, d, J=9.4 Hz), 7.57 (2H, t, J=7.3 Hz), 7.68 (1H, t), 7.78 (2H, d, J=7.6 Hz); m/z ($ES^+$) 361 ($MH^+$). Found: C, 54.29; H, 5.56; N, 5.97. $C_{19}H_{24}N_2O_3S \cdot C_2H_2O_4 \cdot 0.7H_2O$ requires C, 54.46; H, 5.96; N, 6.05%.

EXAMPLE 29 trans-4-Dimethylamino-1-(4-methyl benzenesulphonyl)-1,3,4,5-tetrahydrobenz[cd]indol-5-ol. Hydrogen Oxalate A suspension of (±)-4-azido-3,4-dihydro-1-[(methylphenyl)sulphonyl]benz[cd]indol-5(1H)one (J. Chem. Soc. Perkin Trans. I, 1973, 438–442) (11.9 g) in absolute ethanol (400 ml) and concentrated hydrochloric acid (11.9 ml) was hydrogenated at 25 psi over 10% palladium on carbon (1.2 g) for 6 h. The mixture was diluted with absolute ethanol (300 ml), 10% palladium on carbon (2 g) was added and hydrogenation was resumed for another 16 h at 25 psi. The catalyst was removed by filtration, washed with absolute ethanol (3×125 ml) and the filtrate was concentrated under vacuum. The residue was crystallised from ethanol to give 4.55 g of (±)-4-amino-3,4-dihydro-1-[(methylphenyl)sulphonylbenz[cd]indol-5(1H)one hydrochloride as a white solid.

To a solution of sodium borohydride (1 g) in absolute ethanol (75 ml) was added dropwise via cannula a suspension of the above aminoketone hydrochloride (4.55 g) in absolute ethanol (150 ml) over 15 minutes, keeping the internal temperature below 3° C. The resulting mixture was stirred at −2° C. for 1 h 40 min under nitrogen before it was carefully acidified with 2N hydrochloric acid (28 ml). The ethanol was removed under vacuum and the residue was basified with 2N sodium hydroxide (35 ml). The products were extracted with ethyl acetate (3×150 ml) and the combined organic phases were washed with brine (50 ml), dried ($Na_2SO_4$) and concentrated. Flash chromatography of the residue (silica gel, dichloromethane-ethanol-ammonia, 170:28:3) gave 3.99 g (97%) of 4-amino-1-(4-methyl)benzenesulphonyl-1,3,4,5-tetrahydrobenz[cd]indol-5-ol as a 90:10 mixture of trans and cis isomers; m/z 342 ($M^+$).

A solution of the above aminoalcohol (3.97 g, 11.59 mmol) in absolute ethanol (150 ml), aqueous formaldehyde (38% w/v; 9.2 ml) and glacial acetic acid (92 ml) was hydrogenated at 30 psi over 10% palladium on carbon (1.56 g) for 65 h. The catalyst was filtered off, washed with absolute ethanol and the filtrate was concentrated under vacuum. The residue was dissolved in dichloromethane (40 ml) and washed with 10% aqueous sodium hydrogen carbonate (100 ml). The aqueous layer was extracted with dichloromethane (2×120 ml) and the combined organic phases were dried ($Na_2SO_4$) and concentrated. Flash chromatography of the residue (silica gel, dichloromethane-ethanol-ammonia, 85:15:0 to 1750:225:25) gave 3.68 g (86%) of the title compound free base together with 400 mg of the corresponding cis-isomer. The oxalate salt was prepared from ethanol-diethyl ether; ml) 123°–126° C.; $\delta_H$ (360 MHz, DMSO-$d_6$) 7.86 (2H, d, J=8.4 Hz), 7.76 (1H, d, J=8.1 Hz), 7.55 (1H, s), 7.44–7.36 (3H, m), 7.30 (1H, d, J=7.4 Hz), 5.14 (1H, d, J=9.3 Hz), 3.54–3.38 (1H, m), 3.26–3.16 (1H, m), 3.12–2.96 (1H, m), 2.78 (6H, s), 2.32 (3H, s); m/z (EI) 371 ($M^+$+1). (Found: C, 57.16; H, 5.36; N, 5.99. $C_{20}H_{22}N_2O_3S \cdot 1.0\ C_2H_2O_4$ requires: C, 57.38; H, 5.25; N, 6.08%). [J Chem Soc. Perkin Trans I, 1973, 438–442]

EXAMPLE 30

4-Dimethylamino-5-methoxy-1-(4-methyl benzenesulphonyl)-1,3,4,5-tetrahydro-benz[cd] indole Hydrogen Oxalate To a solution of the product from Example 29 (free base; 700 mg) in anhydrous tetrahydrofuran (10 ml) and anhydrous dimethylformamide (3 ml) was added sodium hydride (60% dispersion in oil; 91 mg) followed, after 10 minutes, by benzyltrimethylammonium chloride (35 mg) and methyl 3-bromopropionate. After stirring at room temperature for 2.5 h, additional sodium hydride was added and stirring was continued for 16 h. Water (50 ml) was added and products were extracted with dichloromethane (3×50 ml), then dried ($MgSO_4$) and concentrated. Flash chromatography of the residue (silica gel, dichloromethane-ethanol, 95:5) gave 30 mg of the title compound free base. The oxalate salt was prepared and crystallised from isopropanol; mp 133°–136° C.; $\delta_H$ (360 MHz, DMSO-$d_6$) 7.86 (2H, d, J=8.4 Hz), 7.80 (1H, d, J=8.1 Hz), 7.52 (1H, s), 7.42–7.34 (3H, m), 7.29 (1H, d, J=7.3 Hz), 4.89 (1H, d, J=6.5 Hz), 3.56–3.48 (4H, m and s), 3.08 (2H, d, J=5.6 Hz), 2.52 (6H, s), 2.31 (3H, s); m/z 384 (M+). (Found: C, 58.01; H, 5.84; N, 5.77. $C_{21}H_{24}N_2O_3S \cdot 1.0\ C_2H_2O_4$ requires: C, 58.22; H, 5.52; N, 5.90%).

What is claimed is:

1. A method for the treatment and/or prevention of a clinical condition for which selective agonism or antagonism of 5-HT$_6$ receptors is indicated comprising administering to a patient in need of such treatment an effective amount of a compound, or a pharmaceutically acceptable salt or prodrug thereof, having a structure in accordance with Formula I or II:

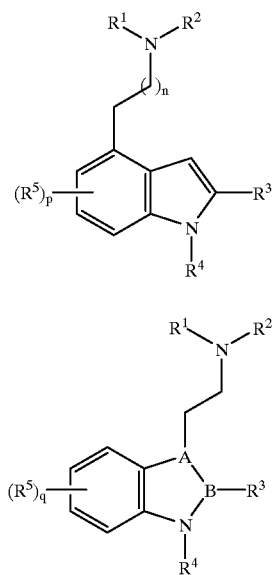

wherein
n is 1 or 2;
p is 0,1,2 or 3;
q is 0,1,2,3 or 4;
$R^1$ and $R^2$ independently represent hydrogen, $C_{1-6}$ alkyl or aryl ($C_{1-6}$)alkyl, or together represent the atoms necessary to complete a heterocycloalkyl group comprising the nitrogen atom to which $R^1$ and $R^2$ are attached;
$R^3$ represents hydrogen, $C_{1-6}$ alkyl, $C_{2-6}$ alkenyl, $C_{2-6}$ alkynyl, aryl($C_{1-6}$)alkyl, aryl, heteroaryl, arylcarbonyl, heteroarylcarbonyl or $C_{1-6}$ alkylcarbonyl;
$R^4$ represents arylsulphonyl, heteroarylsulphonyl, $C_{1-6}$ alkylsulphonyl, di($C_{1-6}$)alkylaminosulphonyl, arylcarbonyl, $C_{1-6}$ alkylcarbonyl, heteroarylcarbonyl or $C_{1-6}$ alkoxycarbonyl;
each $R^5$ independently represents hydroxy, $C_{1-6}$ alkoxy, aryl($C_{1-6}$)alkoxy, nitrile or halogen; and
-A-B- represents —C=C— or —CH—CH—.

2. The method of claim 1 in which said compound is in accordance with said Formula I or II wherein:
$R^1$ and $R^2$ independently represent hydrogen, methyl, ethyl, propyl or benzyl, or $R^1$ and $R^2$ in combination represent pyrrolidinyl, piperidinyl, piperazinyl, 4-methylpiperazinyl or morpholinyl;
$R^3$ represents hydrogen, methyl, ethyl, benzyl, allyl, propargyl, benzoyl, phenyl, thienyl or furoyl;
$R^4$ represents benzenesulphonyl, naphthalene-2-sulphonyl, o-, m- or p-toluenesulphonyl, o-, m- or p-chlorobenzenesulphonyl, o-, m- or p-methoxybenzenesulphonyl, methanesulphonyl, dimethylaminosulphonyl, thienylsulphonyl, benzoyl, acetyl, furoyl or tert-butoxycarbonyl; and $R^5$ represents hydroxy, methoxy, ethoxy, propoxy, benzyloxy, nitrile, fluorine, chlorine or bromine.

3. The method of claim 1 in which the compound is selected from:
(a) compounds of Formula I in which p is zero; $R^1$ and $R^2$ are identical and represent hydrogen or methyl; $R^3$ represents hydrogen or benzoyl; and $R^4$ represents arylsulphonyl or dimethylaminosulphonyl; and
(b) compounds of Formula II in which $R^1$ and $R^2$ are identical and represent hydrogen or methyl, or together complete a pyrrolidinyl, piperidinyl, piperazinyl or 4-methylpiperazinyl ring; $R^3$ represents hydrogen or methyl; $R^4$ represents arylsulphonyl, thienylsulphonyl, benzoyl or tert-butoxycarbonyl; $R^5$ represents hydroxy, methoxy, benzyloxy or nitrile; and q is zero or 1.

4. The method according to claim 1 in which the compound is selected from:
2-[1-(benzenesulphonyl)-1H-indol-4-yl]ethylamine;
N,N-dimethyl 2-[1-(benzenesulphonyl)-1H-indol-4-yl]ethylamine;
N,N-dimethyl 2-[1-(dimethylamino)sulphonyl-1H-indol-4-yl]ethylamine;
N,N-dimethyl 3-[1-(benzenesulphonyl)-1H-indol-4-yl]propylamine; and
N,N-dimethyl 2-[1-(benzenesulphonyl)-2-benzoyl-1H-indol-4-yl]ethylamine;
or pharmaceutically acceptable salts or prodrugs thereof.

5. The method of claim 1 in which the compound is in accordance with Formula II(a):

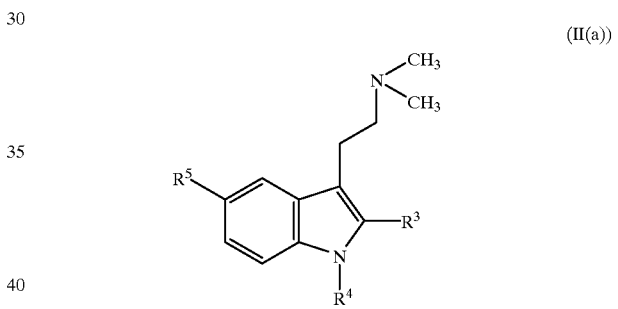

where $R^3$, $R^4$ and $R^5$ are as defined in claim 1.

6. The method of claim 5 in which said compound is selected from:
N,N-dimethyl 2-[1-( benzenesulphonyl)-5-methoxy-1H-indol-3-yl]ethylamine;
N,N-dimethyl 2-[5-methoxy-1-(4-methylbenzenesulphonyl)-1H-indol-3-yl]ethylamine;
N,N-dimethyl 2-[1-(4-chlorobenzenesulphonyl)-5-methoxy-1H-indol-3-yl]ethylamine;
N,N-dimethyl 2-[1-(3-chlorobenzenesulphonyl)-5-methoxy-1H-indol-3-yl]ethylamine;
N,N-dimethyl 2-[5-methoxy-1-(2-naphthalenesulphonyl)-1H-indol-3-yl]ethylamine;
N,N-dimethyl 2-[5-methoxy-1-(4-methoxybenzenesulphonyl)-1H-indol-3-yl]ethylamine;
N,N-dimethyl 2-[1-(2-chlorobenzenesulphonyl)-5-methoxy-1H-indol-3-yl]ethylamine;
N,N-dimethyl 2-(1-benzoyl-5-methoxy-1H-indol-3-yl)ethylamine;
N,N-dimethyl 2-[5-methoxy-1-(2-thiophenesulphonyl)-1H-indol-3-yl]ethylamine;
N,N-dimethyl 2-(1-benzenesulphonyl-5-methoxy-2-methyl-1H-indol-3-yl)ethylamine;
N,N-dimethyl 2-(1-benzenesulphonyl-1H-indol-3-yl)ethylamine;

N,N-dimethyl 2-(1-methylsulphonyl-1H-indol-3-yl)ethylamine;
N,N-dimethyl 2-(5-methoxy-1-methylsulphonyl-1H-indol-3-yl)ethylamine;
[3-(2-dimethylamino-ethyl)-5-hydroxy-1H-indol-1-yl] phenylmethanone;
3-(2-dimethylamino-ethyl)-5-hydroxy-1H-indole-1-carboxylic acid tert-butyl ester;
N,N-dimethyl 2-(1-benzenesulphonyl-5-benzyloxy-1H-indol-3-yl)ethylamine;
N,N-dimethyl 2-(1-benzenesulphonyl-5-hydroxy-1H-indol-3-yl)ethylamine; and
N,N-dimethyl 2-(1- benzenesulphonyl-5-cyano-1H-indol-3-yl)ethylamine;
and pharmaceutically acceptable salts or prodrugs thereof.

7. The method of claim 1 in which the compound is in accordance with Formula II(b):

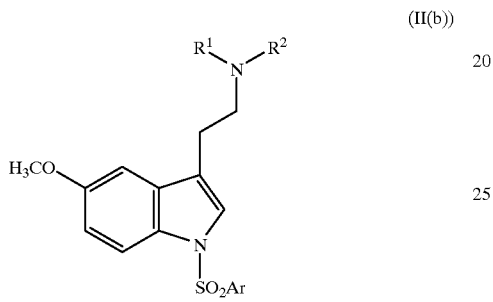

where $R^1$ and $R^2$ are as defined in claim 1, and Ar represents an aryl group.

8. The method of claim 7 in which said compound is selected from:
2-[1-(benzenesulphonyl)-5-methoxy-1H-indol-3-yl] ethylamine;
1-benzenesulphonyl-5-methoxy-3-[(2-pyrrolidin-1-yl)ethyl] 1H-indole;
1-benzenesulphonyl-5-methoxy-3-[(2-piperizin-1-yl)ethyl]-1H-indole; and
1-benzenesulphonyl-5-methoxy-3-[(2-piperazin-1-yl)ethyl]-1H-indole
and pharmaceutically acceptable salts or prodrugs thereof.

9. The method of claim 1 in which the compound is in accordance with Formula II(c):

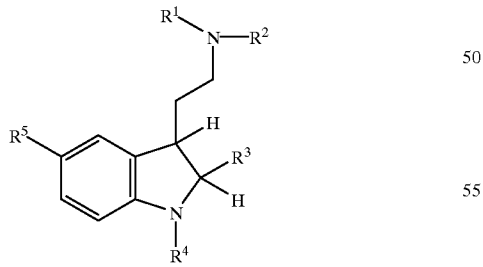

where $R^1$–$R^5$ are as defined in claim 1.

10. The method of claim 9 in which said compound is:
N,N-dimethyl 2-(1-benzenesulphonyl-5-methoxy-2,3-dihydro-1H-indol-3-yl)ethylamine;
or a pharmaceutically acceptable salt or prodrug thereof.

11. The method of claim 1 in which the compound has a 5-$HT_6$ receptor (rat or human) binding affinity (Ki), when measured in cell lines expressing cloned recombinant 5-$HT_6$ receptors, of less than 1 μM, and has a selective affinity for 5-$HT_6$ receptors relative to 5-$HT_5$ and/or 5-$HT_7$ receptors of at least 3-fold.

12. The method of claim 1 in which the clinical condition is selected from the group consisting of:
Parkinson's disease, Huntingdon's disease, anxiety, depression, manic depression, psychosis, epilepsy, obsessive compulsive disorders, migraine, Alzheimers disease, sleep disorders, feeding disorders, panic attacks, withdrawal from drug abuse, schizophrenia, disorders associated with spinal trauma and/or head injury, hydrocephalus, and GI (gastrointestinal) disorders.

13. A compound of Formula I:

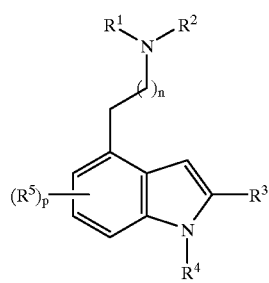

wherein
n is 1 or 2;
p is 0,1,2 or 3;
$R^1$ and $R^2$ independently represent hydrogen, $C_{1-6}$ alkyl or aryl ($C_{1-6}$)alkyl, or together represent the atoms necessary to complete a heterocycloalkyl group comprising the nitrogen atom to which $R^1$ and $R^2$ are attached;
$R^3$ represents hydrogen, $C_{1-6}$ alkyl, $C_{2-6}$ alkenyl, $C_{2-6}$ alkynyl, aryl($C_{1-6}$)alkyl, aryl, heteroaryl, arylcarbonyl, heteroarylcarbonyl or $C_{1-6}$ alkylcarbonyl;
$R^4$ represents arylsulphonyl, heteroarylsulphonyl, $C_{1-6}$ alkylsulphonyl, di($C_{1-6}$)alkylaminosulphonyl, arylcarbonyl, $C_{1-6}$ alkylcarbonyl, heteroarylcarbonyl or $C_{1-6}$ alkoxycarbonyl; and
each $R^5$ independently represents hydroxy, $C_{1-6}$ alkoxy, aryl($C_{1-6}$)alkoxy, nitrile or halogen,
or a pharmaceutically acceptable salt or prodrug thereof.

14. A compound according to claim 13 in which $R^1$ and $R^2$ independently represent hydrogen, methyl, ethyl, propyl or benzyl, or $R^1$ and $R^2$ in combination represent pyrrolidinyl, piperidinyl, piperazinyl, 4-methylpiperazinyl or morpholinyl;
$R^3$ represents hydrogen, methyl, ethyl, benzyl, allyl, propargyl, benzoyl, phenyl, thienyl or furoyl;
$R^4$ represents benzenesulphonyl, naphthalene-2-sulphonyl, o-, m- or p-toluenesulphonyl, o-, m- or p-chlorobenzenesulphonyl, o-, m- or p-methoxybenzenesulphonyl, methanesulphonyl, dimethylaminosulphonyl, thienylsulphonyl, benzoyl, acetyl, furoyl or tert-butoxycarbonyl; and
$R^5$ represents hydroxy, methoxy, ethoxy, propoxy, benzyloxy, nitrile, fluorine, chlorine or bromine.

15. A compound according to claim 13 in which p is zero; $R^1$ and $R^2$ are identical and represent hydrogen or methyl; $R^3$ represents hydrogen or benzoyl; and $R^4$ represents arylsulphonyl or dimethylaminosulphonyl.

16. A compound according to claim 15 selected from:
2-[1-(benzenesulphonyl)-1H-indol-4-yl]ethylamine;
N,N-dimethyl 2-[1-(benzenesulphonyl)-1H-indol-4-yl]ethylamine;
N,N-dimethyl 2-[1-(dimethylamino)sulphonyl-1H-indol-4-yl]ethylamine;
N,N-dimethyl 3-[1-(benzenesulphonyl)-1H-indol-4-yl]propylamine;
N,N-dimethyl 2-[1-(benzenesulphonyl)-2-benzoyl-1H-indol-4-yl]ethylamine;
and pharmaceutically acceptable salts and prodrugs thereof.

17. A pharmaceutical composition comprising a compound according to claim 13 in association with a pharmaceutically acceptable carrier.

18. A method for the treatment and/or prevention of a clinical condition for which selective agonism or antagonism of 5-HT6 receptors is indicated comprising administering to a patient in need of such treatment an effective amount of a compound, or a pharmaceutically acceptable salt or prodrug thereof, having a structure in accordance with Formula I as defined in claim 13.

19. The method of claim 12 in which the clinical condition is selected from anorexia, bulimia, abuse of cocaine, ethanol, nicotine, and benzodiazepines, and irritable bowel syndrome.

* * * * *

(12) EX PARTE REEXAMINATION CERTIFICATE (5815th)
United States Patent
Pineiro et al.

(10) Number: US 6,187,805 C1
(45) Certificate Issued: Jul. 17, 2007

(54) INDOLE AND INDOLINE DERIVATIVES AS 5-HT$_6$ SELECTIVE LIGANDS

(75) Inventors: Jose Luis Castro Pineiro, Bishops Stortford (GB); George McAllister, Bishops Stortford (GB); Michael Geoffrey Neil Russel, Welwyn Garden City (GB)

(73) Assignee: Merck Sharp & Dohme Ltd., Hoddesdon (GB)

Reexamination Request:
No. 90/006,381, Sep. 13, 2002

Reexamination Certificate for:
Patent No.: 6,187,805
Issued: Feb. 13, 2001
Appl. No.: 09/392,406
Filed: Sep. 9, 1999

(30) Foreign Application Priority Data

Sep. 15, 1998 (GB) .............................. 9820113

(51) Int. Cl.
*C07D 209/00* (2006.01)
*C07D 209/08* (2006.01)
*C07D 209/14* (2006.01)
*C07D 209/16* (2006.01)
*C07D 209/12* (2006.01)
*C07D 209/90* (2006.01)
*C07D 409/00* (2006.01)
*C07D 409/12* (2006.01)
*A61K 31/403* (2006.01)
*A61K 31/4045* (2006.01)

(52) U.S. Cl. ............... 514/415; 514/235.2; 514/254.09; 514/323; 514/414; 544/143; 544/373; 546/201; 548/467; 548/469; 548/491

(58) Field of Classification Search .................. 548/503
See application file for complete search history.

(56) References Cited

U.S. PATENT DOCUMENTS

| | | | |
|---|---|---|---|
| 3,478,054 A | 11/1969 | Pattison et al. | 260/326.12 |
| 3,481,953 A | 12/1969 | Herbst | 260/326.12 |
| 3,852,452 A | * 12/1974 | Bruderlein et al. | 514/214.01 |
| 3,901,916 A | * 8/1975 | Bastian et al. | 548/411 |
| 3,914,379 A | * 10/1975 | Szarvasi et al. | 514/444 |
| 4,463,208 A | * 7/1984 | Cragoe et al. | 562/462 |
| 4,748,113 A | * 5/1988 | Marshall | 435/12 |
| 4,845,118 A | * 7/1989 | Lang et al. | 514/338 |
| 4,870,085 A | 9/1989 | Glaser et al. | 514/323 |
| 5,084,454 A | * 1/1992 | Varasi et al. | 514/230.5 |
| 5,252,580 A | * 10/1993 | Takahashi et al. | 514/292 |
| 5,474,547 A | * 12/1995 | Aebischer et al. | 604/891.1 |
| 5,532,237 A | * 7/1996 | Gallant et al. | 514/235.2 |
| 6,200,957 B1 | * 3/2001 | Goulet et al. | 514/19 |

FOREIGN PATENT DOCUMENTS

| | | |
|---|---|---|
| RO | 77049 | 7/1981 |
| WO | 9213856 | 8/1992 |
| WO | 9827081 | 6/1998 |

OTHER PUBLICATIONS

Persons et al., European Journal of Medicinal Chemistry (1991), 26(4), pp. 473–475.*

Cannon et al., Journal of Medicinal Chemistry, (1984), 27(3), pp. 386–389.*

Cerletti et al., Advances in Pharmacology (New York), (1968), 6(Pt. B), pp. 233–246.*

Michael G. N. Russell, et al, "N–Arylsulfonylindole Derivatives as Serotonin 5–HT6 Receptor Ligands", J. Med. Chem. 2001, 44, pp. 3881–3895.

Elaine Sanders–Bush et al. "5–Hydroxytryptamine (Serotonin): Receptor Agonists and Antagonists", Goodman & Gilman's, The Pharmacological Basis of Therapeutics, Eleventh Edition, p. 297–315.

Floyd E. Bloom, "Neurotransmission and the Central Nervous System", Goodman & Gilman's, The Pharmacological Basis of Therapeutics, Eleventh Edition, p. 336–338.

Alex S. Evers et al., "General Anesthetics", Goodman & Gilman's, The Pharmacological Basis of Therapeutics, Eleventh Edition, p. 341–368.

Sarbu et al., "New Indole Derivatives with Biological Activities," Revue Romaine de Chimie, 25, 2 p. 245–51 (1980).

Sleight et al., "The 5–HT6 receptor: A new target for the treatment of CNS disorders," Serotonin ID research alert, 1997 2(3): 115–118.

Glennon et al., "Influence of Amine Substituents on 5–HT2A versus 5–HT2C Binding of Phenylalkyl– and Indolylalkylamines," J. Med. Chem., 1994, 37, 1929–1935.

Fuji et al., "Preparation of Alkyl–Substituted Indoles in the Benzene Portion. Part 6. Synthetic Procedure for 4–, 5–, 6–, or 7–Alkoxy– and Hydroxyindole Derivatives," Chem. Pharm. Bull. 40(9) 2344–2352 (1992).

\* cited by examiner

*Primary Examiner*—Evelyn Mei Huang

(57) ABSTRACT

Three classes of indole and indoline derivatives are disclosed as ligands selective for the 5-HT$_6$ receptors, and hence of value in the treatment or prevention of CNS disorders, including Alzheimer's disease, Parkinson's disease, schizophrenia, depression and anxiety. A particular class, 1-substituted-4-(ω-N,N-dialkyl-aminoalkyl)indoles, are claimed as novel compounds.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 12 is cancelled.

Claims 1–3, 6, 8–9, 13–14 and 19 are determined to be patentable as amended.

Claims 4–5, 7, 10–11 and 15–18, dependent on an amended claim, are determined to be patentable.

1. A method for the treatment and/or prevention of a clinical condition for which selective agonism or antagonism of 5-HT$_6$ receptors is indicated comprising administering to a patient in need of such treatment an effective amount of a compound, or a pharmaceutically acceptable salt or prodrug thereof, having a structure in accordance with Formula I or II:

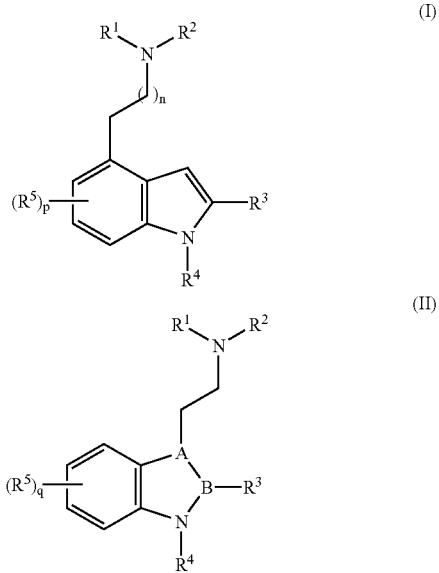

wherein
n is 1 or 2;
p is 0,1,2 or 3;
q is 0,1,2,3 or 4;
R$^1$ and R$^2$ independently represent hydrogen, C$_{1-6}$ alkyl or aryl (C$_{1-6}$)alkyl [, or together represent the atoms necessary to complete a heterocycloalkyl group comprising the nitrogen atom to which R$^1$ and R$^2$ are attached];
R$^3$ represents hydrogen, C$_{1-6}$ alkyl, C$_{2-6}$ alkenyl, C$_{2-6}$ alkynyl, aryl(C$_{1-6}$)alkyl, aryl, heteroaryl, arylcarbonyl, heteroarylcarbonyl or C$_{1-6}$ alkylcarbonyl;

R$^4$ represents arylsulphonyl, heteroarylsulphonyl, C$_{1-6}$ alkylsulphonyl, di(C$_{1-6}$)alkylaminosulphonyl, [arylcarbonyl,] C$_{1-6}$ alkylcarbonyl, [heteroarylcarbonyl] or C$_{1-6}$ alkoxycarbonyl;
each R$^5$ independently represents hydroxy, C$_{1-6}$ alkoxy, aryl(C$_{1-6}$)alkoxy, nitrile or halogen; and
-A-B- represents —C=C— or —CH—CH—;
*Wherein any alkyl or aryl group represented by R$^1$–R$^5$ and any alkyl or aryl moiety of any group represented by R$^1$–R$^5$ is optionally substituted by one or more substituent groups independently selected from C$_{1-6}$ alkyl, halogen, hydroxyl, and C$_{1-6}$ alkoxy;*
*Wherein the clinical condition for which selective agonism or antagonism of 5-HT$_6$ receptors is indicated is selected from the group consisting of: Parkinson's disease, Huntingdon's disease, depression, manic depression, psychosis, epilepsy, obsessive compulsive disorders, migraine, Alzheimers disease, sleep disorders, feeding disorders, panic attacks, withdrawal from drug abuse, and schizophrenia.*

2. The method of claim 1 in which said compound is in accordance with said Formula I or II wherein:
R$^1$ and R$^2$ independently represent hydrogen, methyl, ethyl, propyl or benzyl [, or R$^1$ and R$^2$ in combination represent pyrrolidinyl, piperidinyl, piperazinyl, 4-methylpiperazinyl or morpholinyl];
R$^3$ represents hydrogen, methyl, ethyl, benzyl, allyl, propargyl, benzoyl, phenyl, thienyl or furoyl;
R$^4$ represents benzenesulphonyl, naphthalene-2-sulphonyl, o-, m- or p-toluenesulphonyl, o-, m- or p-chlorobenzenesulphonyl, o-, m- or p-methoxybenzenesulphonyl, methanesulphonyl, dimethylaminosulphonyl, thienylsulphonyl, [benzoyl,] acetyl, [furoyl] or tert-butoxycarbonyl; and
R$^5$ represents hydroxy, methoxy, ethoxy, propoxy, benzyloxy, nitrile, fluorine, chlorine or bromine.

3. The method of claim 1 in which the compound is selected from:
(a) compounds of Formula I in which p is zero; R$^1$ and R$^2$ are identical and represent hydrogen or methyl; R$^3$ represents hydrogen or benzoyl; and R$^4$ represents arylsulphonyl or dimethylaminosulphonyl; and
(b) compounds of Formula II in which R$^1$ and R$^2$ are identical and represent hydrogen or methyl [, or together complete a pyrrolidinyl, piperidinyl, piperazinyl or 4-methylpiperazinyl ring]; R$^3$ represents hydrogen or methyl; R$^4$ represents arylsulphonyl, thienylsulphonyl, [benzoyl] or tert-butoxycarbonyl; R$^5$ represents hydroxy, methoxy, benzyloxy or nitrile; and q is zero or 1.

6. The method of claim [5] *1* in which said compound is selected from:
N,N-dimethyl 2-[1-(benzenesulphonyl)-5-methoxy-1H-indol-3-yl]ethylamine;
N,N-dimethyl 2-[5-methoxy-1-(4-methylbenzenesulphonyl)-1H-indol-3-yl]ethylamine;
N,N-dimethyl 2-[1-(4-chlorobenzenesulphonyl)-5-methoxy-1H-indol-3-yl]ethylamine;
N,N-dimethyl 2-[1-(3-chlorobenzenesulphonyl)-5-methoxy-1H-indol-3-yl]ethylamine;
N,N-dimethyl 2-[5-methoxy-1-(2-naphthalenesulphonyl)-1H-indol-3-yl]ethylamine;
N,N-dimethyl 2-[5-methoxy-1-(4-methoxybenzenesulphonyl)-1H-indol-3-yl]ethylamine;

N,N-dimethyl 2-[1-(2-chlorobenzenesulphonyl)-5-methoxy-1H-indol-3-yl]ethylamine;

[N,N-dimethyl 2-(1-benzoyl-5-methoxy-1H-indol-3-yl)ethylamine;]

N,N-dimethyl 2-[5-methoxy-1-(2-thiophenesulphonyl)-1H-indol-3-yl]ethylamine;

N,N-dimethyl 2-(1-benzenesulphonyl-5-methoxy-2-methyl-1H-indol-3-yl)ethylamine;

N,N-dimethyl 2-(1-benzenesulphonyl-1H-indol-3-yl)ethylamine;

N,N-dimethyl 2-(1-methylsulphonyl-1H-indol-3-yl)ethylamine;

N,N-dimethyl 2-(5-methoxy-1-methylsulphonyl-1H-indol-3-yl)ethylamine;

[[3-(2-dimethylamino-ethyl)-5-hydroxy-1H-indol-1-yl]phenylmethanone;]

3-(2-dimethylamino-ethyl)-5-hydroxy-1H-indole-1-carboxylic acid tert-butyl ester;

N,N-dimethyl 2-(1-benzenesulphonyl-5-benzyloxy-1H-indol-3-yl)ethylamine;

N,N-dimethyl 2-(1-benzenesulphonyl-5-hydroxy-1H-indol-3-yl)ethylamine; and

N,N-dimethyl 2-(1-benzenesulphonyl-5-cyano-1H-indol-3-yl)ethylamine;

and pharmaceutically acceptable salts or prodrugs thereof.

8. The method of claim 7 in which said compound is [selected from:]

2-[1-(benzenesulphonyl)-5-methoxy-1H-indol-3-yl]ethylamine[;

1-benzenesulphonyl-5-methoxy-3-[(2-pyrrolidin-1-yl)ethyl]-1H-indole;

1-benzenesulphonyl-5-methoxy-3-[(2-piperidin-1-yl)ethyl]-1H-indole; and 1-benzenesulphonyl-5-methoxy-3-[(2-piperazin-1-yl)ethyl]-1H-indole]

[and] or a pharmaceutically acceptable [salts] salt or [prodrugs] prodrug thereof.

9. [The method of claim 1 in which the compound is] *A method for the treatment and/or prevention of a clinical condition for which selective agonism or antagonism of 5-HT₆ receptors is indicated comprising administering to a patient in need of such treatment an effective amount of a compound, or a pharmaceutically acceptable salt or prodrug thereof, having a structure* in accordance with Formula II(c):

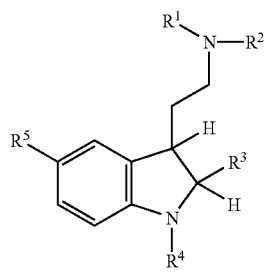

(II(c))

[where R¹–R⁵ are defined in claim 1.] *wherein:*

R¹ *and R² independently represent hydrogen, C₁₋₆ alkyl or aryl (C₁₋₆)alkyl, or together represent the atoms necessary to complete a heterocycloalkyl group comprising the nitrogen atom to which R¹ and R² are attached;*

R³ *represents hydrogen, C₁₋₆ alkyl, C₂₋₆ alkenyl, C₂₋₆ alkynyl, aryl(C₁₋₆)alkyl, aryl, heteroaryl, arylcarbonyl, heteroarylcarbonyl or C₁₋₆ alkylcarbonyl;*

R⁴ *represents arylsulphonyl, heteroarylsulphonyl, C₁₋₆ alkylsulphonyl, di(C₁₋₆)alkylaminosulphonyl, arylcarbonyl, C₁₋₆ alkylcarbonyl, heteroarylcarbonyl or C₁₋₆ alkoxycarbonyl; and*

R⁵ *represents hydroxy, C₁₋₆ alkoxy, aryl(C₁₋₆)alkoxy, nitrile or halogen.*

13. A compound of Formula I:

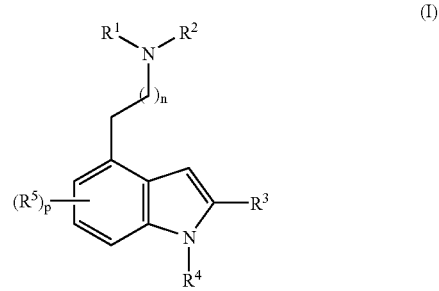

(I)

wherein n is 1 or 2;

p is 0,1,2 or 3;

R¹ and R² independently represent hydrogen, C₁₋₆ alkyl or aryl (C₁₋₆)alkyl, or together represent the atoms necessary to complete a heterocycloalkyl group comprising the nitrogen atom to which R¹ and R² are attached;

R³ represents hydrogen, C₁₋₆ alkyl, C₂₋₆ alkenyl, C₂₋₆ alkynyl, aryl(C₁₋₆)alkyl, aryl, heteroaryl, arylcarbonyl, heteroarylcarbonyl or C₁₋₆ alkylcarbonyl;

R⁴ represents arylsulphonyl, heteroarylsulphonyl, C₁₋₆ alkylsulphonyl, di(C₁₋₆)alkylaminosulphonyl, arylcarbonyl, [C₁₋₆ alkylcarbonyl,] heteroarylcarbonyl or C₁₋₆ alkoxycarbonyl, *with the proviso that R⁴ is not 4-toluenesulphonyl when R¹ and R² are both n-propyl*; and each R⁵ independently represents hydroxy, C₁₋₆ alkoxy, aryl(C₁₋₆)alkoxy, nitrile or halogen, or a pharmaceutically acceptable salt or prodrug thereof.

14. A compound according to claim 13 in which R¹ and R² independently represent hydrogen, methyl, ethyl, propyl or benzyl, or R¹ and R² in combination represent pyrrolidinyl, piperidinyl, piperazinyl, 4-methylpiperazinyl or morpholinyl;

R³ represents hydrogen, methyl, ethyl, benzyl, allyl, propargyl, benzoyl, phenyl, thienyl or furoyl;

R⁴ represents benzenesulphonyl, naphthalene-2-sulphonyl, o-, m- or p-toluenesulphonyl, o-, m- or p-chlorobenzenesulphonyl, o-, m- or p-methoxybenzenesulphonyl, methanesulphonyl, dimethylaminosulphonyl, thienylsulphonyl, benzoyl, [acetyl], furoyl or tert-butoxycarbonyl; and R⁵ represents hydroxy, methoxy, ethoxy, propoxy, benzyloxy, nitrile, fluorine, chlorine or bromine.

19. The method of claim [12] *1* in which the clinical condition is selected from anorexia, bulimia, abuse of cocaine, ethanol, nicotine, and benzodiazepines, and irritable bowel syndrome.

* * * * *